(12) United States Patent
Van Duyne et al.

(10) Patent No.: US 10,271,780 B2
(45) Date of Patent: Apr. 30, 2019

(54) COMBINED SURFACE ENHANCED AND SPATIALLY OFFSET RAMAN SPECTROSCOPY FOR BIOMOLECULE DETECTION

(75) Inventors: Richard P. Van Duyne, Wilmette, IL (US); Matthew R. Glucksberg, Chicago, IL (US); Joseph T. Walsh, Jr., Evanston, IL (US); Jonathan M. Yuen, Chicago, IL (US); Nilam C. Shah, Chicago, IL (US)

(73) Assignee: Northwestern University, Evanston, IL (US)

( * ) Notice: Subject to any disclaimer, the term of this patent is extended or adjusted under 35 U.S.C. 154(b) by 2133 days.

(21) Appl. No.: 13/303,815

(22) Filed: Nov. 23, 2011

(65) Prior Publication Data

US 2015/0051459 A1 Feb. 19, 2015

Related U.S. Application Data

(60) Provisional application No. 61/416,547, filed on Nov. 23, 2010.

(51) Int. Cl.
| | |
|---|---|
| A61B 5/1455 | (2006.01) |
| A61B 5/145 | (2006.01) |
| G01N 21/65 | (2006.01) |
| A61B 5/1459 | (2006.01) |

(52) U.S. Cl.
CPC .......... *A61B 5/1459* (2013.01); *A61B 5/1455* (2013.01); *A61B 5/14532* (2013.01); *G01N 21/658* (2013.01)

(58) Field of Classification Search
CPC ... A61B 5/1455; A61B 5/0091; A61B 5/0075; A61B 5/0059

USPC .................................................. 600/310–344
See application file for complete search history.

(56) References Cited

U.S. PATENT DOCUMENTS

| | | | |
|---|---|---|---|
| 2006/0054506 A1 | 3/2006 | Natan et al. | |
| 2009/0118605 A1* | 5/2009 | Van Duyne et al. | 600/365 |
| 2009/0219523 A1* | 9/2009 | Morris et al. | 356/300 |
| 2010/0087723 A1 | 4/2010 | Van Duyne et al. | |

(Continued)

FOREIGN PATENT DOCUMENTS

| | | |
|---|---|---|
| WO | 2008/122035 | 10/2008 |

OTHER PUBLICATIONS

Bashkatov et al., "Optical properties of human skin, subcutaneous and mucous tissues in the wavelength range from 400 to 2000nm," J Phys D: Appl Phys, 38: 2543-2555, 2005.

(Continued)

*Primary Examiner* — Eric F Winakur
*Assistant Examiner* — Marjan Fardanesh
(74) *Attorney, Agent, or Firm* — Casimir Jones SC; David W. Staple

(57) ABSTRACT

The present invention provides systems and methods employing a surface enhanced Raman biosensor and sensing devices for collecting spatially offset Raman spectra from the biosensor. In certain embodiments, the present invention provides systems and methods for quantifying the concentration of an analyte in a subject, and/or identifying the presence or absence of an analyte in a subject, from a plurality of spatially offset Raman spectra generated from a surface enhanced Raman biosensor implanted in a subject.

20 Claims, 8 Drawing Sheets

(56) References Cited

U.S. PATENT DOCUMENTS

2010/0145200 A1    6/2010    Mahadevan-Jansen et al.

OTHER PUBLICATIONS

Blanco Gomis et al., "Determination of monosaccharides in cider by reversed-phase liquid chromatography," J Anal Chim Acta, 436: 173-180, 2001.

Boisselier et al., "Gold nanoparticles in nanomedicine: preparations, imaging, diagnostics, therapies and toxicity," Chem Soc Rev, 38: 1759-1782, 2009.

Brauker J. "Continuous glucose sensing: future technology developments," Diabetes Technol Ther, 11 (Suppl 1): S25-S36, 2009.

Feng et al., "Gold nanoparticle based surface-enhanced Raman scattering spectroscopy of cancerous and normal nasopharyngeal tissues under near-infrared laser excitation," Appl Spectrosc, 63: 1089-1094, 2009.

Gilligan et al., "Feasibility of continuous long-term glucose monitoring from a subcutaneous glucose sensor in humans," Diabetes Technol Ther, 6(3):378-86, 2004.

Huang et al., "Shining light on the microbial world the application of Raman microspectroscopy," Adv Appl Microbiol, 70: 153-186, 2010.

International Search Report and Written Opinion for PCT Application No. PCT/US2011/062057, dated May 2, 2012.

Kaufman et al., "A pilot study of the continuous glucose monitoring system: clinical decisions and glycemic control after its use in pediatric type 1 diabetic subjects," Diabetes Care, 24: 2030-2034, 2001.

Kneipp et al., "Novel optical nanosensors for probing and imaging live cells," Nanomedicine: NBM, 6: 214-226, 2010.

Kondepati et al., "Recent progress in analytical instrumentation for glycemic control in diabetic and critically ill patients," Anal Bioanal Chem, 388: 545-563, 2007.

Lyandres et al., "Progress toward an in vivo surface-enhanced Raman spectroscopy glucose sensor," Diabetes Technol Ther, 10: 257-265, 2008.

Lyandres et al., "Real-time glucose sensing by surface-enhanced Raman spectroscopy in bovine plasma facilitated by a mixed decanethiol/mercaptohexanol partition layer," Anal Chem, 77: 6134-6139, 2005.

Matousek et al., "Deep non-invasive Raman spectroscopy of living tissue and powders," Chem Soc Rev, 36: 1292-1304, 2007.

Matousek et al., "Emerging concepts in deep Raman spectroscopy of biological tissue," Analyst, 134: 1058-1066, 2009.

Matousek et al., "Subsurface probing in diffusely scattering media using spatially offset Raman spectroscopy," Appl Spectro, 59: 393-400, 2005.

McHugh et al., "Selective functionalisation of TNT for sensitive detection by SERRS," Chem Commun, 6:580-581, 2002.

Nielsen et al., "The optics of human skin: Aspects important for human health," Solar Radiation and Human Health; Bjertness E., Ed., The Norwegian Academy of Science and Letters: Oslo, 35-46, 2008.

Oliver et al., "Glucose sensors: a review of current and emerging technology," Diabet Med, 26: 197-210, 2009.

Qian et al., "In vivo tumor targeting and spectroscopic detection with surface-enhanced Raman nanoparticle tags," Nat Biotechnol, 26: 83-90, 2008.

Russell et al., "A fluorescence-based glucose biosensor using concanavalin A and dextran encapsulated in a poly (ethylene glycol) hydrogel," Anal Chem, 71: 3126-3132, 1999.

Shafer-Peltier et al., "Toward a glucose biosensor based on surface-enhanced Raman scattering," J Am Chem Soc, 125: 588-593, 2003.

Stuart et al., "Glucose sensing using near-infrared surface-enhanced Raman spectroscopy: gold surfaces, 10-day stability, and improved accuracy," Anal Chem, 77: 4013-4019, 2005.

Stuart et al., "In vivo glucose measurement by surface-enhanced Raman spectroscopy," Anal Chem, 78: 7211-7215, 2006.

Sylvia et al., "Surface-enhanced raman detection of 2,4-dinitrotoluene impurity vapor as a marker to locate landmines," Anal Chem, 72: 5834, 2000.

Taranenko et al., "Surface-Enhanced Raman Detection of Nerve Agent Simulant (DMMP and DIMP) Vapor on Electrochemically Prepared Silver Oxide Substrates," J Raman Spec, 27: 379-384, 1996.

Vo Dinh et al., "Surface-enhanced Raman Scattering (SERS) method and instrumentation for genomics and biomedical analysis," J Raman Spec, 30: 785-793, 1999.

Weissenbacher et al., "Continuous surface enhanced Raman spectroscopy for the detection of trace organic pollutants in aqueous systems," J Mol Struct, 410-411:539-542, 1997.

Yang et al., "Applications of "Wired" Peroxidase Electrodes for Peroxide Determination in Liquid Chromatography Coupled to Oxidase Immobilized Enzyme Reactors," Anal Chem, 67: 1326-1331, 1995.

Yonzon et al., "A glucose biosensor based on surface-enhanced Raman scattering: improved partition layer, temporal stability, reversibility, and resistance to serum protein interference," Anal Chem, 76: 78-85, 2004.

Yuen et al., "Transcutaneous glucose sensing by surface-enhanced spatially offset Raman spectroscopy in a rat model," Anal Chem, 82: 8382-8385, 2010.

Zavaleta et al., "Multiplexed imaging of surface enhanced Raman scattering nanotags in living mice using noninvasive Raman spectroscopy," Proc Natl Acad Sci USA, 106: 13511-13516, 2009.

\* cited by examiner

COMBINED SURFACE ENHANCED AND SPATIALLY OFFSET RAMAN SPECTROSCOPY FOR BIOMOLECULE DETECTION

CROSS-REFERENCE TO RELATED APPLICATION

The present invention claims priority to U.S. Provisional Patent Application Ser. Nos. 61/416,547 filed Nov. 23, 2010, which is hereby incorporated by reference in its entirety.

GOVERNMENT SUPPORT

This invention was made with government support under Grant No. 5R56DK078691-02 awarded by the National Institutes of Health, Grant No. CHE-0911145 awarded by the National Science Foundation, and Grant No. FA9550-08-1-0221 awarded by the Air Force Office of Scientific Research/DARPA. The government has certain rights in the invention.

FIELD OF THE INVENTION

The present invention relates to systems and methods employing a surface enhanced Raman biosensor and sensing devices for collecting spatially offset Raman spectra from the biosensor. In certain embodiments, the present invention provides systems and methods for quantifying the concentration of an analyte in a subject, and/or identifying the presence or absence of an analyte in a subject, from a plurality of spatially offset Raman spectra generated from a surface enhanced Raman biosensor implanted in a subject (e.g., implanted immediately under the skin).

BACKGROUND

In diabetes mellitus, the body either fails to produce or to respond to insulin, which regulates glucose metabolism, resulting in large fluctuations in glucose levels. These fluctuations can cause a range of secondary complications, including kidney disease, heart disease, blindness, nerve damage, and gangrene. Current treatment of diabetes consists of self-regulation of blood glucose levels through frequent monitoring and a combination of diet, medication, and insulin injection, depending on the type of diabetes. Most patients measure their glucose levels by withdrawing small samples of blood using a "finger-stick" apparatus followed by electrochemical detection of an oxidation product of glucose. This type of measurement is both painful and inconvenient. As a result, many patients fail to adequately monitor their glucose levels, risking secondary complications. A faster, easier, and less painful method for frequently measuring glucose levels would be of great individual, clinical, and societal benefit. Continuous monitoring of blood glucose would open the door to feedback control of implanted insulin pumps. A reliable and robust sensor technology is the single stumbling block in an artificial pancreas.

SUMMARY OF THE INVENTION

The present invention provides systems and methods employing a surface enhanced Raman biosensor and sensing devices for collecting spatially offset Raman spectra from the biosensor. In certain embodiments, the present invention provides systems and methods for quantifying the concentration of an analyte in a subject, and/or identifying the presence or absence of an analyte in a subject, from a plurality of spatially offset Raman spectra generated from a surface enhanced Raman biosensor implanted in a subject.

In some embodiments, the present invention provides method for quantification and/or detection of an analyte in vivo, comprising: a) acquiring a plurality of spatially offset Raman spectra from a biosensor implanted in a subject (e.g., immediately under the skin), wherein the biosensor comprises a plurality of nanobiosensors, wherein the nanobiosensors comprise a plurality of nanospheres and a metal film over the nanospheres; and b) quantifying the concentration of an analyte in the subject based on the plurality of spatially offset Raman spectra; and/or c) identifying the presence or absence of an analyte signature from the plurality of spatially offset Raman spectra, thereby identifying the presence or absence of the analyte in the subject. In certain embodiments, the biosensor further comprises a substrate, and wherein said plurality of nanobiosensors are adherent to said substrate.

In certain embodiments, the acquiring step comprises the steps of: (1) illuminating the biosensor at at least one first spot with light; (2) collecting Raman scattering light from the biosensor at a plurality of second spots in response to illumination by the light, wherein each second spot is apart from the at least one first spot so as to define a source-detection (S-D) offset distance. In some embodiments, the S-D offset distance is smaller than 50 mm (e.g., 5-45 mm, 10-40 mm, 15-35 mm, 20-30 mm, about 10 mm, about 20 mm, about 30 mm, about 40 mm, or about 45 mm). In further embodiments, the light illuminating the biosensor is a coherent light generated from a laser. In some embodiments, the acquiring step is performed with at least one of a spectrograph and a CCD camera.

In particular embodiments, the acquiring step is performed with a probe having a working end and in-line filters placed on the working end. In some embodiments, the probe comprises: (a) at least one first fiber positioned over the at least one first spot for delivering the light thereto; and (b) at least one second fiber. In further embodiments, the probe comprises: (a) at least one first fiber positioned over the at least one first spot for delivering the light thereto; and (b) at least one second fiber translationally movable from one to another of the plurality of second spots for collecting the Raman scattering light therefrom. In other embodiments, the probe comprises: (a) at least one first fiber positioned over the at least one first spot for delivering the light thereto; and (b) a plurality of second fibers spatially arranged surrounding the at least one first fiber, each second fiber adapted for collecting the Raman scattering light from a corresponding second spot. In additional embodiments, the probe comprises a fiber array having: (a) at least one first fiber; and (b) a plurality of second fibers, wherein the at least one first fiber and the plurality of second fibers spatially arranged in a row or in a matrix form, wherein the at least one first fiber is adapted for delivering the light to the at least one first spot, and wherein the plurality of second fibers is adapted for collecting the Raman scattering light from the plurality of second spots. In other embodiments, the probe comprises a fiber array having: (a) at least one first fiber; and (b) a plurality of second fibers spatially arranged in a radial ring form originated from the at least one first fiber, wherein the at least one first fiber is adapted for delivering the light to the at least one first spot, and wherein the plurality of second fibers is adapted for collecting the Raman scattering light from the plurality of second spots.

In certain embodiments, the methods further comprise the step of acquiring a Raman spectrum from the at least one first spot illuminated with the light. In particular embodiments, the biosensor is fully implanted in the subject (i.e., no part of the biosensor is projecting outside of the body through the skin). In other embodiments, the biosensor is implanted under the skin of the subject (e.g., immediately under the skin between the muscle layer and skin layer).

In some embodiments, the present invention provides systems comprising: a) a surface enhanced Raman biosensor configured to be implanted in a subject, wherein the biosensor comprises a plurality of nanobiosensors, wherein the nanobiosensors comprise a plurality of nanospheres and a metal film over the nanospheres; and b) a sensing device configured for collecting spatially offset Raman spectra from the biosensor when the biosensor is implanted in a subject. In particular embodiments, the biosensor further comprises a substrate, and wherein said plurality of nanobiosensors are adherent to said substrate.

In certain embodiments, the systems further comprise: c) a light source capable of illuminating the biosensor through tissue of the subject. In other embodiments, the sensing device comprises a spectrograph and/or CCD camera. In additional embodiments, the sensing devices comprises a probe a having a working end and in-line filters placed on the working end.

In particular embodiments, the biosensor further comprises a self-assembled partition layer formed on the surface of the metal film over the nanospheres. In other embodiments, the self-assembled partition layer comprising at least two compounds. In some embodiments, the self-assembled partition layer comprises a hydrophilic compound and a hydrophobic compound. In further embodiments, the hydrophilic compound and the hydrophobic compound comprise modified alkanes. In other embodiments, the alkanes comprise a chain length of at least 5 carbon atoms. In some embodiments, the hydrophobic compound comprises decanethiol and the hydrophilic compound comprises mercaptohexanol.

In certain embodiments, the substrate is copper or titanium. In other embodiments, the substrate is configured to provide a plurality of nanowells containing the nanospheres. In some embodiments, the nanospheres comprise polystyrene or silica nanospheres. In other embodiments, wherein the biosensor further comprises a receptor specific for the analyte, wherein the receptor is configured to bind reversibly to the analyte. In particular embodiments, the analyte is glucose or other biomolecule detectable in blood.

In other embodiments, the substrate comprises copper or titanium. In particular embodiments, the substrate is configured to provide a plurality of nanowells containing the nanospheres. In some embodiments, the nanospheres comprise polystyrene or silica nanospheres. In additional embodiments, the biosensors further comprise a receptor specific for the analyte, wherein the receptor is configured to bind reversibly to the analyte. In certain embodiments, the analyte is glucose or other analyte detectable in blood.

In some embodiments, the nanobiosensors are coated with a noble metal (e.g., silver, gold, platinum, etc. and combinations thereof). In some embodiments, the nanobiosensors are configured for quantitative detection of the analyte. In some embodiments, the nanobiosensors are configured for use in vivo (e.g., including, but not limited to, implantation of the nanobiosensor under the skin or in the eye). In some embodiments, the nanobiosensors comprise a biocompatible coating. In some embodiments, the nanobiosensors are configured for detection of an analyte in a bodily fluid. In some embodiments, the analyte is glucose. In some embodiments, the analyte is selected from the group consisting of ascorbate, lactic acid, urea, pesticides, chemical warfare agents, pollutants, and explosives, although the systems may be used for the detection of any type of analyte. In some embodiments, the nanobiosensors further comprise a surface bound reversibly-binding analyte receptor, the receptor specific for the analyte of interest. In some embodiments, the analyte is glucose and the reversibly-binding receptor is concanavalin A.

In other embodiments, the nanobiosensors further comprise a self-assembled monolayer formed on the surface of the nanobiosensors. In some embodiments, the self-assembled monolayer is selected from the group consisting of 4-aminothiophenol, L-cystein, 3-mercaptopropionic acid, 11-mercaptoundecanoic acid, 1-hexanethiol, 1-octanethiol, 1-decanethiol (1-DT), 1-hexadecanethiol, mercaptoethanol, poly-DL-lysine, 3-mercapto-1-propanesufonic acid, benzenethiol, and cyclohexylmercaptan. In other embodiments, the self-assembled monolayer is a combination of two or more components. In some preferred embodiments, the self-assembled monolayer is 1-DT. In other embodiment, the self-assembled monolayer is (1-mercaptoundeca-11-yl)tri(ethylene glycol) $(HS(CH_2)_{11}(OCH_2CH_2)_3OH$. In some embodiments, the nanobiosensors are embedded in nanowells. In some embodiments, the nanowells are fabricated out of silica.

In some embodiments, the nanobiosensors are configured for quantitative detection of glucose or other analytes in a physiological concentration range (e.g., 0-450 mg/dL). In some embodiments, the nanobiosensors are capable of quantitative detection of glucose or other analytes at the low end of the physiological concentration range (e.g., 0-100 mg/dL). In some embodiments, the nanobiosensors are capable of quantitative detection of glucose or other analytes at the high end of the physiological concentration range (e.g., 200-450 mg/dL). In some embodiments, the nanobiosensors are configured for detection of the analyte for at least 3 days (e.g., >3 days, >4 days, >5 days, >1 week, >2 weeks, >1 month, or more). In some embodiments, the nanobiosensors are configured for reversible detection of the analyte. In certain embodiments, the nanobiosensors are configured for detection of the analyte in the presence of interfering molecules, for example, proteins.

In some embodiments, the detection devices comprise delivery and collection optics, a laser source, a notch filter, and a detector. In some embodiments, the delivery and collection optics and the notch filter are incorporated into a fiber optic probe. In some embodiments, the fiber optic probe is in communication with the laser source and the detector. In some embodiments, the system further comprises a second device configured for the delivery of insulin or other agents to a subject.

In some embodiments, nanobiosensors and devices described herein are configured for quantitative detection of glucose or other analytes based on a single calibration. In some embodiments, nanobiosensors and devices described herein are configured for quantitative detection of glucose or other analytes without recalibration. In some embodiments, nanobiosensors and devices described herein are configured for quantitative detection of glucose or other analytes with limited recalibration (e.g., <1/day . . . <1/week . . . <1/month . . . etc.).

In some embodiments, the present invention provides methods, systems, and devices for the in vivo quantification, detection, and/or monitoring of one or more analytes (e.g., glucose) in the blood of a subject. In some embodiments, a subject is a human, primate, mammal, or other mammal. In some embodiments, a subject suffers from, or is suspected of suffering from, diabetes (type I, type II, gestational, etc.).

DEFINITIONS

Figure 1:
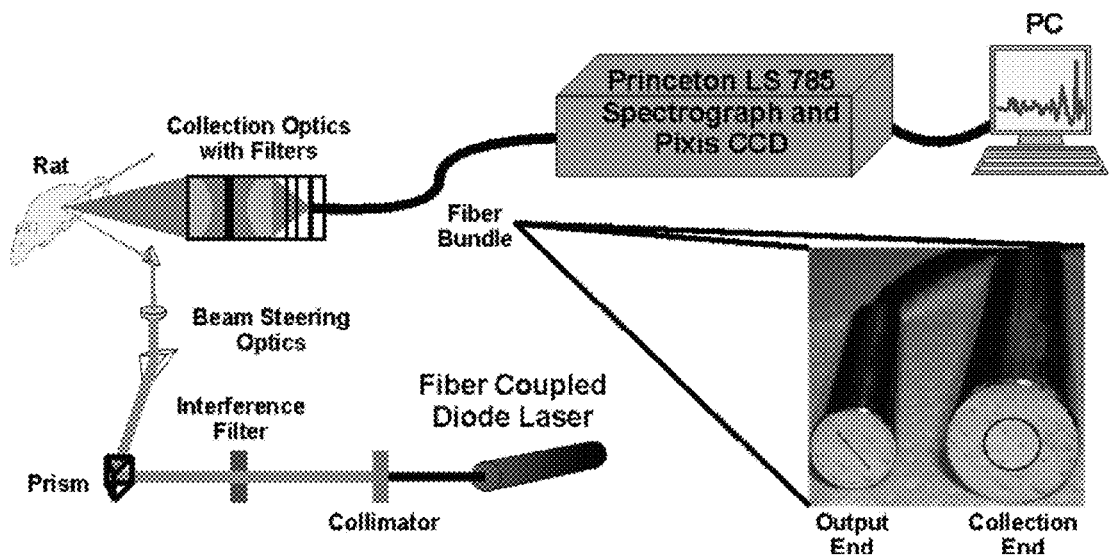
FIG. 1 shows a schematic diagram of an exemplary SESORS apparatus. Inset shows annular fiber bundle used to achieve offset collection.

As used herein, the term "nanobiosensors," refers to any sensor that is small enough to be implanted internally (e.g., under the skin or in the eye), is specific for detection of one or more analytes, and is capable of having an altered surface enhanced Raman signal in the presence of the specific analyte(s). In preferred embodiments, the nanobiosensors comprise components for specifically, but reversibly, interacting with the specific analyte.

As used herein, the term "surface bound reversibly-binding receptor" refers to a receptor bound to the surface of a nanobiosensor of the present invention that binds reversibly to a specific analyte. In preferred embodiments, the interaction of the receptor and the analyte lasts long enough for detection of the analyte by the sensor.

As used herein, the term "self-assembled monolayer" refers to a material that forms single layer or multilayers of molecules on the surface of a nanobiosensor. As used herein, the term "self-assembled partition layer" refers to material that forms a layer or multilayers on the surface of a nanobiosensor.

As used herein, the term "nanowell" refers to a solid surface comprising wells for immobilizing the nanobiosensors of the present invention. In preferred embodiments, the nanowells are made of an inert material and are large enough to hold a plurality of nanobiosensors.

As used herein, the term "bodily fluid" refers to any fluid normally found in the body of a mammal (e.g., a human). Exemplary bodily fluids include, but are not limited to, blood, serum, lymph, aqueous humor, interstitial fluid, and urine. The term "bodily fluid" encompasses both bodily fluid found in its natural state (e.g., in the body) and bodily fluid removed from the body.

As used herein, the term "analyte" refers to any molecule or atom or molecular complex suitable for detection by the nanobiosensors of the present invention. Exemplary analytes include, but are not limited to, various biomolecules (e.g., proteins, nucleic acids, lipids, etc.), glucose, ascorbate, lactic acid, urea, pesticides, chemical warfare agents, pollutants, and explosives.

As used herein, the term "physiological concentration range" refers to the concentration range of an analyte that is typically found in an animal (e.g., a human). The physiological concentration range covers both the physiological concentration in a healthy animal and in an animal with a disease (e.g., diabetes).

As used herein, the term "detection of said analyte for at least 3 days" refers to nanobiosensors of the present invention that are capable of detecting an analyte for at least 3 days in vitro or in vivo. Detection of said analyte for at least 3 days does not require that the nanobiosensor take continuous measurements for 3 days, but that the sensor functions (e.g., by taking periodic measurements) for at least 3 days. In preferred embodiments, the measurements are quantitative and maintain precision and accuracy for at least 3 days.

As used herein, the term "reversible detection of said analyte" refers to nanobiosensors of the present invention that are capable of repeated detection of an analyte. For example, in some embodiments, nanobiosensors measure the concentration of glucose in a biological fluid multiple times (e.g., from one time per second to one time per hour) over the course of the usable life span of the sensor (e.g., at least 3 days).

As used herein, the term "detection of said analyte in the presence of interfering proteins" refers to nanobiosensors of the present invention that are able to function in the presence of proteins other than the analyte (e.g., biological proteins).

As used herein, the term "biological macromolecule" refers to large molecules (e.g., polymers) typically found in living organisms. Examples include, but are not limited to, proteins, nucleic acids, lipids, and carbohydrates.

As used herein, the term "polymer" refers to material comprised of repeating subunits. Examples of polymers include, but are not limited to polyacrylamide and poly (vinyl chloride), poly(vinyl chloride) carboxylated, and poly (vinyl chloride-co-vinyl acetate co-vinyl) alcohols.

As used herein, the term "polymerization" encompasses any process that results in the conversion of small molecular monomers into larger molecules consisting of repeated units. Typically, polymerization involves chemical cross-linking of monomers to one another.

As used herein, the term "spectrum" refers to the distribution of electromagnetic energies arranged in order of wavelength.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

DETAILED DESCRIPTION

The present invention provides systems and methods employing a surface enhanced Raman biosensor and sensing devices for collecting spatially offset Raman spectra from the biosensor. In certain embodiments, the present invention provides systems and methods for quantifying the concentration of an analyte in a subject, and/or identifying the presence or absence of an analyte in a subject, from a plurality of spatially offset Raman spectra generated from a surface enhanced Raman biosensor implanted in a subject.

As described in the Examples below, in certain embodiments, the present invention provides quantitative, in vivo, transcutaneous biomolecule measurements using surface enhanced Raman spectroscopy (SERS). In the Examples below, silver film over nanosphere surfaces were functionalized with a mixed self-assembled monolayer (SAM) and implanted subcutaneously in a Sprague-Dawley rat. The glucose concentration was monitored in the interstitial fluid. SER spectra were collected from the sensor chip through the skin using spatially offset Raman spectroscopy (SORS). The combination of SERS and SORS is a powerful new approach to the challenging problem of in vivo metabolite and drug sensing and can be used to detect other types of biomolecules.

The field of surface enhanced Raman spectroscopy (SERS) research has undergone a renaissance in the last decade, especially in the area of biological applications, due to the great advances made in the fabrication of large area, reproducible, long-lived SERS substrates. Biological applications of SERS ranging from cancer detection (Boisselier, E.; Astruc, D. *Chemical Society Reviews* 2009, 38, 1759-1782; Feng, S. Y.; Lin, J. Q.; Cheng, M.; Li, Y. Z.; Chen, G. N.; Huang, Z. F.; Yu, Y.; Chen, R.; Zeng, H. S. *Applied Spectroscopy* 2009, 63, 1089-1094; herein incorporated by reference in their entireties) to the study of basic cell processes (Huang, W. E.; Li, M. Q.; Jarvis, R. M.; Goodacre, R.; Banwart, S. A In *Advances in Applied Microbiology, Vol 70*; Elsevier Academic Press Inc: San Diego, 2010; Vol. 70, pp 153-186; Kneipp, J; Kneipp, H.; Wittig, B.; Kneipp, K. *Nanomedicine-Nanotechnology Biology and Medicine* 2010, 6, 214-226; herein incorporated by reference in their entireties) have been vigorously pursued. However, most of this work has been carried out in vitro, due to the challenges posed by the complexity of the in vivo environment. These include: (1) placement of the SERS-active surface in vivo; (2) the numerous interferants that can potentially adsorb to the SERS-active surface rendering it unresponsive to glucose or other target analytes; and (3) the natural inflammation and foreign body response (FBR) that occurs.

The majority of in vivo SERS work has been qualitative in nature and has used SERS as an alternative to fluorescence labeling (Qian, X. M.; Peng, X. H.; Ansari, D.O.; Yin-Goers, Q.; Chen, G. Z.; Shin, D. M.; Yang, L.; Young, A N.; Wang, M. D.; Nie, S. M, *Nature Biotechnology* 2008, 26, 83-90; Zavaleta, C. L.; Smith, B. R; Walton, I.; Doering, W.; Davis, G.; Shojaei, B.; Natan, M. I; Gambhir, S. S. *Proceedings of the National Academy of Sciences of the United States of America* 2009, 106, 13511-13516; herein incorporated by reference in their entireties). Previously, it was demonstrated that SERS can be used in vivo to directly and quantitatively detect biological targets. Some researchers have pursued approaches with an implantable SERS glucose sensor (Lyandres, O.; Yuen, J. M.; Shah, N. C.; VanDuyne, R P.; Walsh, J. T; Glucksberg, M. R *Diabetes Technology & Therapeutics* 2008, 10, 257-265; Shafer-Peltier, K. E.; Haynes, C. L.; Glucksberg, M. R.; Van Duyne, R. P. *Journal of the American Chemical Society* 2003, 125, 588-593; Shah, N. C.; Lyandres, O.; Yonzon, C. R; Walsh, J. T.; Glucksberg, M. R; Van Duyne, R. P. *Analytical Chemistry* 2005, 77, 6134-6139; Stuart, D. A.; Yonzon, C. R.; Zhang, X.; Lyandres, O.; Shah, N. C.; Glucksberg, M. R; Walsh, J. T.; VanDuyne, R. P. *Analytical Chemistry* 2005, 77, 4013-4019; Stuart, D. A; Yuen, J.; Shah, N. C.; Lyandres, O.; Yonzon, C. R; Glucksberg, M. R.; Walsh Jr., J. T.; Van Duyne, R. P. *Anal. Chem* 2006; Yonzon, C. R.; Haynes, C. L.; Zhang, X. Y.; Walsh, J. T.; Van Duyne, R. P. *Analytical Chemistry* 2004, 76, 78-85; herein incorporated by reference in their entireties). The SERS sensor utilizes the ability of Raman spectroscopy to specifically detect glucose and mitigates the inherently low intensity of Raman scattering by using surface enhancement to amplify the intensity by factors of $10^6$-$10^8$. In previous in vivo studies, a dorsal skinfold chamber was implanted in a rat for optical access to the sensor (Lyandres, O.; Yuen, J. M.; Shah, N. C.; VanDuyne, R P.; Walsh, J. T.; Stuart, D. A; Yuen, J.; Shah, N. C.; Lyandres, O.; Yonzon, C. R; Glucksberg, M. R.; Walsh Jr., J. T.; Van Duyne, R. P. *Anal. Chem* 2006; herein incorporated by reference in their entireties). A windowed chamber was the only method available that allowed spectra collection from the sensor.

The solution provided by embodiments of the present invention removes the window and directly collect the SERS spectra transcutaneously. However, introducing the skin into the optical detection system presents a new set of challenges that have been overcome by the present invention. The large refractive index change between skin and air immediately produces light intensity losses due to back reflections (Yonzon, C. R.; Haynes, C. L.; Zhang, X. Y.; Walsh, J. T.; Van Duyne, R. P. *Analytical Chemistry* 2004, 76, 78-85; herein incorporated by reference in its entirety). Within the skin layers, light is further attenuated due to multiple scattering and absorption events. These can be caused by lipids in cell walls, which scatter, blood, which absorbs, and proteins such as keratin and melanin which can both scatter and absorb light (Bashkatov, A. N.; Genina, E. A.; Kochubey, V. I.; Tuchin, V. V. *Journal of Physics D-Applied Physics* 2005, 38, 2543-2555; Nielsen, K.; Zhao, L. S., JJ; Stamnes, K.; Moam, J. In *Solar Radiation and Human Health*; Bjertness, E., Ed.; The Norvegian Academy of Science and Letters: Oslo, 2008; herein incorporated by reference in their entireties). These difficulties are further compounded when illuminating and collecting from a subcutaneous sample since both the input laser excitation light must pass through the skin and the output Raman scattered light must pass back out through the skin to reach the detector. The present invention addresses these issues with the use of spatially offset Raman spectroscopy (SORS) (Matousek, P.; Clark, I. P.; Draper, E. R. C.; Morris, M. D.; Goodship, A. E.; Everall, N.; Towrie, M.; Finney, W. F.; Parker, A. W. *Applied Spectroscopy* 2005, 59, 393-400; herein incorporated by reference in its entirety).

In SORS, Raman scattered light is collected from regions offset from the point of laser excitation at the sample (Matousek, P.; Clark, I. P.; Draper, E. R. C.; Morris, M. D.; Goodship, A. E.; Everall, N.; Towrie, M.; Finney, W. F.; Parker, A. W. *Applied Spectroscopy* 2005, 59, 393-400; see also U.S. Pat. Pub. 2010/0145200, herein incorporated by reference in its entirety). In contrast, for normal Raman spectroscopy the excitation and collection points are coincident so that the surface of the sample gives the greatest contribution to the Raman spectrum. When spectra are collected some distance away from the excitation point, spectral features originating from underlying layers give greater contribution than the surface (Matousek, P. *Chemical Society Reviews* 2007, 36, 1292-1304; Matousek, P.; Stone, N. *Analyst* 2009, 134, 1058-1066; herein incorporated by reference in their entireties). Combining the sensitivity of SERS with the depth resolution of SORS yields a powerful new tool for biomedical sensing.

In certain embodiments, the SERS biosensors of the present invention are coated with a noble metal. In some embodiments, the metal is silver. The present invention, is not limited to the use of silver. Any noble metal may be utilized, including, but not limited to, gold and platinum. In certain embodiments, a 1 nm layer of titanium and/or chromium substrate is added to the surface of the particles prior to the silver in order to improve the adhesion of the silver to the surface. In some embodiments a nanosphere solution (e.g., commercially available nanosphere solution) is directly added to the titanium and/or chromium substrate. In some embodiments, nanospheres are purified and/or isolated prior to addition to titanium and/or chromium substrate and/or noble metal. In some embodiments, purification and/or isolation comprise: centrifugation and removal from supernatent, dialysis, column chromatography purification, sucrose gradient purification, or any suitable method of purifying nanospheres. In some embodiments, nanospheres are dispersed in water (e.g., deionized water, ultrapure water) following isolation and/or purification.

To prolong analyte interaction with the noble metal nanoparticle surface, in some embodiments, a reversibly-binding receptor is used to temporarily bind the analyte to the surface. In the case of glucose, in some embodiments a receptor such as concanavalin A is used as a reversible-binding agent (See e.g., Russell et al., Ana. Chem. 71:3126 [1999], herein incorporated by reference) and/or an alkanethiol, such as 1-decanethiol, is used to form the self-assembled capture layer (Blanco Gomis et al., J. Anal. Chim. Acta 436:173 [2001]; Yang et al., Anal. Chem. 34:1326 [1995], both of which are herein incorporated by reference). Other exemplary capture molecules include longer-chained alkanethiols, cyclohexyl mercaptan, glucosamine, boronic acid and mercapto carboxylic acids (e.g., 11-mercaptoundecanoic acid). In other embodiments, apo-glucose oxide is used as the capture molecule.

Alternatively, a self-assembled monolayer (SAM) is formed on the nanoparticle surface to concentrate the analyte of interest near the nanoparticle surface, an adaptation of common high performance liquid chromatography technology. Exemplary SAMs include, but are not limited to, 4-aminothiophenol, L-cystein, 3-mercaptopropionic acid, 11-mercaptoundecanoic acid, 1-hexanethiol, 1-octanethiol, 1-DT, 1-hexadecanethiol, poly-DL-lysine, 3-mercapto-1-propanesulfonic acid, benzenethiol, and cyclohexylmercaptan. In preferred embodiments, the SAM is comprised of straight chain alkanethiols. In some particularly preferred embodiments, the SAM is 1-decanethiol. In other particularly preferred embodiments, the SAM is EG3. In still further embodiments, the SAM is a thiolated boronic acid. In yet other embodiments, the SAM is polyethylene glycol (PEG) or a thiolated PEG derivative. Preferred SAMs are those that efficiently and reversibly bind analytes but have capture and release kinetic rapid enough to follow fast changes in analyte levels (e.g., physiological glucose levels). In particularly preferred embodiments, the SAM comprises mixed components, for example, DT/MH (decanethiol/mercaptohexanol). In other embodiments, the SAM is modified to substitute a halogen, for example fluorine, for hydrogen.

In some embodiments, a dialysis membrane is utilized to exclude molecules significantly larger than the analyte (e.g., glucose) from contacting the nanoparticle surface. The present invention is not limited to a particular mechanism. Indeed, an understanding of the mechanism is not necessary to understand the present invention. Nonetheless, it is contemplated that the exclusion of large molecules will increase the accuracy and precision of measurement of small molecule analytes such as glucose.

In other embodiments, nanoparticles are coated to prevent the accumulation of interfering proteins on the particle surface. In some embodiments, PEG is immobilized on nanoparticle surfaces to prevent protein fouling. In some embodiments, silica sensor surfaces not coated with silver are PEGylated with silane terminated monomethoxy-PEG and silver coated nanoparticle surfaces are coated with oligoethyleneglycol terminated alkanethiols. In some embodiments, the PEGylated surfaces are analyzed using X-ray photoelectron spectroscopy and secondary ion mass spectra to determine the presence and homogeneity of PEG on surfaces. In some embodiments, protein adhesion to modified surfaces is measured by placing sensors in a culture of fibroblasts for several weeks, removing unattached cells, and counting the number of adhered cells. In some embodiments, the skin implant sensor is based on a simple chip implant that can include a $SiO_2$ substrate. In other embodiments, the eye sensor is adapted for incorporation into an intraocular by etching nanowells directly into the intraocular lens surface. The choice of excitation wavelength is optimized for data collection in the eye and the skin.

In some embodiments, the present invention provides a nanobiosensor for use in the detection of analytes. In some preferred embodiments, the sensor is a surface-enhanced Raman (SERS) nanobiosensor. The in vivo biochemical sensor of the present invention is designed to take advantage of the surface-enhancing properties of noble metallic nanoparticles to acquire spatially offset Raman spectra from eye (e.g., aqueous humor) or skin (e.g., interstitial fluid, blood), or other organs.

The surface-enhanced Raman nanobiosensor enables real-time, continuous measurement of multiple analytes (such as glucose, urea, and ascorbate) simultaneously. Another advantage of this technique is that it directly detects the presence of the analytes, rather than relying on an indirect measurement. In some embodiments, the initial placement of the sensor requires surgery, but once in place subsequent measurements are non-invasive.

In some embodiments, the sensor is fabricated from a substrate including, but not limited to, polymethacrylate, acrylic, or silicone for the eye and $SiO_2$ for under the skin. In some embodiments, noble metal nanoparticles are deposited into shallow wells in the substrate. In preferred embodiments, the sensor region is only a few millimeters in its longest dimension. In some embodiments, the particles are then coated with a self-assembled monolayer (SAM) to protect them from fouling and to prolong interaction between the analytes of interest and the surface. In some embodiments, reversibly-binding receptors are incorporated into this SAM. The sensor is implanted either under the skin or used to replace the intraocular lens. To detect surface-enhanced Raman signals from the sensor, delivery and collection optics as well as a laser source, an optical filter, and a detector are used. In some embodiments, the delivery and collection optics (as well as filters) are incorporated into a fiber optic probe, which is connected to the laser and detector.

In some embodiments, the eye implant is a modified intraocular lenses commonly used in lens replacements when cataracts occur. The noble metal nanoparticles are incorporated into a small portion of these lenses to form the sensor.

In some embodiments, for skin implant sensor fabrication, the noble metal nanoparticles are deposited in shallow wells in a chip (e.g., only a few millimeters in its longest dimension) composed of $SiO_2$.

In some embodiments, the surface-enhanced Raman nanobiosensors of the present invention enable faster, easier, and continuous measurement of glucose levels for diabetics. In other embodiments, the nanobiosensors are used in the measurement of previously unmonitored analytes critical in other diseases. Continuous measurements of blood glucose levels open the door to implanted insulin pumps. In some embodiments, a SERS nanobiosensor is used for monitoring drug-delivery in many situations, enabling tighter control over drug administration.

The methods of the present invention are not limited to the detection of glucose. Previously, SERS has been used to detect a wide variety of analytes present at low concentrations, including, but not limited to, pollutants (Weissenbacher et al., J. Mol. Struct. 410-411:539 [1997]), explosives (McHugh et al., Chem. Commun. 580:-581 [2002]; Sylvia et al., Anal. Chem. 72:5834 [2000]), chemical warfare agents (Taranenko et al., J. Raman Spec. 27:379 [1996]), and DNA (Vo Dinh et al., J. Raman Spec. 30:785 [1999]). The methods of the present invention are thus applicable to the in vivo detection of exposure (e.g., monitoring) of individuals exposed to such agents.

In some embodiments, the present invention provides kits and systems for use in monitoring the level of an analyte in an individual. In some embodiments, the kits are kits for home use by a subject (e.g., a subject with diabetes). For example, in some embodiments, a sensor is implanted under the skin or the eye of a subject (e.g., by a medical professional) and the subject is provided with a device for monitoring levels of analyte (e.g., the subject places the device near the sensor and the device reads-out glucose levels). The subject can then use this information to maintain better control of blood glucose levels and avoid complications of the disease.

In other embodiments, the present invention provides kits for use by medical professionals. For example, in some embodiments, the present invention provides kits for monitoring military personnel in a war situation where they may be exposed to toxins. The sensors are implanted prior to potential exposure (e.g., prior to departing for active duty). Personnel are then monitored by medical professionals using a detection device.

In still further embodiments, the present device is used at home or by a medical professional to monitor exposure to pesticides (e.g., in agricultural workers). The workers receive a sensor and are then monitored using a detection device.

In yet other embodiments, the present invention provides systems comprising nanobiosensors and detection devices. For example, in some embodiments, the systems are combined with an insulin delivery device (e.g., an insulin pump) for use as an artificial pancreas. Such a device finds use in the treatment of individuals with diabetes who require regular insulin doses. In some embodiments, the device takes readings from a sensor (e.g., implanted in the skin near the device), calculates blood glucose concentration, and administers an appropriate level of insulin. In other embodiments, the entire system is internal (e.g., implanted underneath the skin or located in the abdominal cavity). In some embodiments, the entire system is a single unit comprising a sensor, a detection device, and an insulin delivery device.

EXPERIMENTAL

The following examples serve to illustrate certain preferred embodiments and aspects of the present invention and are not to be construed as limiting the scope thereof.

Example 1

Combination of SERS and SORS for In Vivo Transcutaneous Glucose Measurements

This example describes quantitative, in vivo, transcutaneous glucose measurements using surface enhanced Raman spectroscopy (SERS). Silver film over nanosphere surfaces were functionalized with a mixed self-assembled monolayer (SAM) and implanted subcutaneously in a Sprague-Dawley rat. The glucose concentration was monitored in the interstitial fluid. SER spectra were collected from the sensor chip through the skin using spatially offset Raman spectroscopy (SORS).

Materials. All the chemicals were reagent grade or better and used as purchased. Silver pellets (99.99%) were purchased from Kurt J. Lesker Co. (Clairton, Pa.). Titanium was obtained from McMaster-Carr (Chicago, Ill.) and cut into 18-mm-diameter disks. $H_2SO_4$, 95.5-96.5% was purchased from EMD chemicals, $NH_4OH$, $H_2O_2$, and ethanol were purchased from Fisher Scientific (Fairlawn, Va.). Silica nanosphere solution (600 nm±10-15% diameter, 10.2% solid) was purchased from Bangs Laboratories, Inc. (Fishers, Ind.). Only Ultrapure water (18.2 MΩ $cm^{-1}$) from a Millipore system (Marlborough, Mass.) was used. Glucose, decanethiol (DT), and 6-mercapto-1-hexanol (MH) were purchased from Sigma-Aldrich (St. Louis, Mo.).

AgFON fabrication and incubation procedure. The titanium substrates were soaked in 6:1 $H_2O/H_2SO_4$ for two minutes, rinsed, and sonicated in a 5:1:1 H20/30% $H_2O_2$/$NH_4OH$ solution for ten minutes. Approximately 10 ul of nanosphere solution was drop-coated onto clean titanium substrates and allowed to dry under ambient conditions. 200 nm thick Ag films were deposited over the nanosphere layer using a home built thermal deposition system to form AgFON substrates. The substrates were incubated in 1 mM DT in ethanol for 45 minutes and transferred to 1 mM MH in ethanol for at least 12 hours to form a mixed DT/MH SAM. The AgFONs were kept in the 1 mM MH solution until used.

Instrumentation. The SORS system (FIG. 1) was adapted from that described by Matousek (20, herein incorporated by reference in its entirety). A fiber coupled diode laser ($\lambda$ex=785 om, P=60 mW, Newport Corp., Irvine, Calif.) was used as the illumination source and an interference filter (Semrock, Rochester, N.Y.) isolated the laser line. Optical quality prisms and mirrors (Thor Labs, Newton, N.J.) were used to guide the laser to the sample. Identical lenses (D=50.8 mm, f=60.0 mm, Thor Labs) were used to collect the scattered light and focus it into the fiber bundle. Between the lenses, a notch filter (Semrock, Rochester, N.Y.) was used to reject the Raleigh scattered light. Between the second focusing lens and the fiber bundle another notch filter and long pass filter (Semrock, Rochester, N.Y.) were used to further exclude the elastically scattered light.

The fiber bundle was a custom made bundle (C-Technologies, Bridgewater, N.J.) composed of 26 fibers arranged in a 6 mm diameter circle at the collection, head and aligned vertically at the detection end (FIG. 1 inset). The Raman spectrometer was an Acton LS785 spectrograph paired with a Pixis 400BR CCD camera (princeton Instruments, Trenton, N.J.). Replacing the custom fiber bundle with a standard fiber bundle allowed the SORS system to function as a conventional Raman spectroscopy system.

In vivo transcutaneous SESORS. A Sprague-Dawley rat was anesthetized with isoflurane (1.53%) throughout the surgical procedure and the duration of the experiment. The animal was checked for pain reactions by toe-tug and blink tests. None were observed. After the anesthetic had taken effect, the side and belly of the animal were shaved and chemically depilated. An incision was made in the skin and a pocket was blunt dissected into the subcutaneous space. The AgFON was placed in the pocket and the incision was closed with surgical clips. The rat was placed in the SORS apparatus and SESORS spectra were acquired ($\lambda ex=785$ nm, P=50 mW, time=20 sec).

In vivo transcutaneous SESORS glucose measurements. Experiments were conducted to gauge the viability of transcutaneous SESORS as a data collection technique for glucose measurements. The femoral vein and artery of anesthetized rats were cannulated using PE 50 tubing for drug/glucose injections and blood glucose measurements, respectively. All incisions were shut with surgical clips and the rat was placed in the SORS system. Following the experiment, the animals were sacrificed with an overdose of sodium pentabarbitol (150 mglkg) and bilateral thorachotomy. Glucose was varied in the rat through intermittent intravenous infusion over the course of the experiment. A bolus of glucose was delivered at a concentration of 1 g/mL in sterile phosphate buffered saline. A droplet of blood was drawn from the rat, the glucose level was measured with the Ascensia Elite home blood glucometer, and corresponding SESORS measurements were taken ($\lambda ex=785$ nm, P=50 mW, time=2 min). To keep the osmotic pressure of the rat at normal physiological levels, a volume of BSA equal to the blood removed was injected following each blood glucose measurement. The data were collected and analyzed by the partial least squares leave-one-out method.

Figure 2:
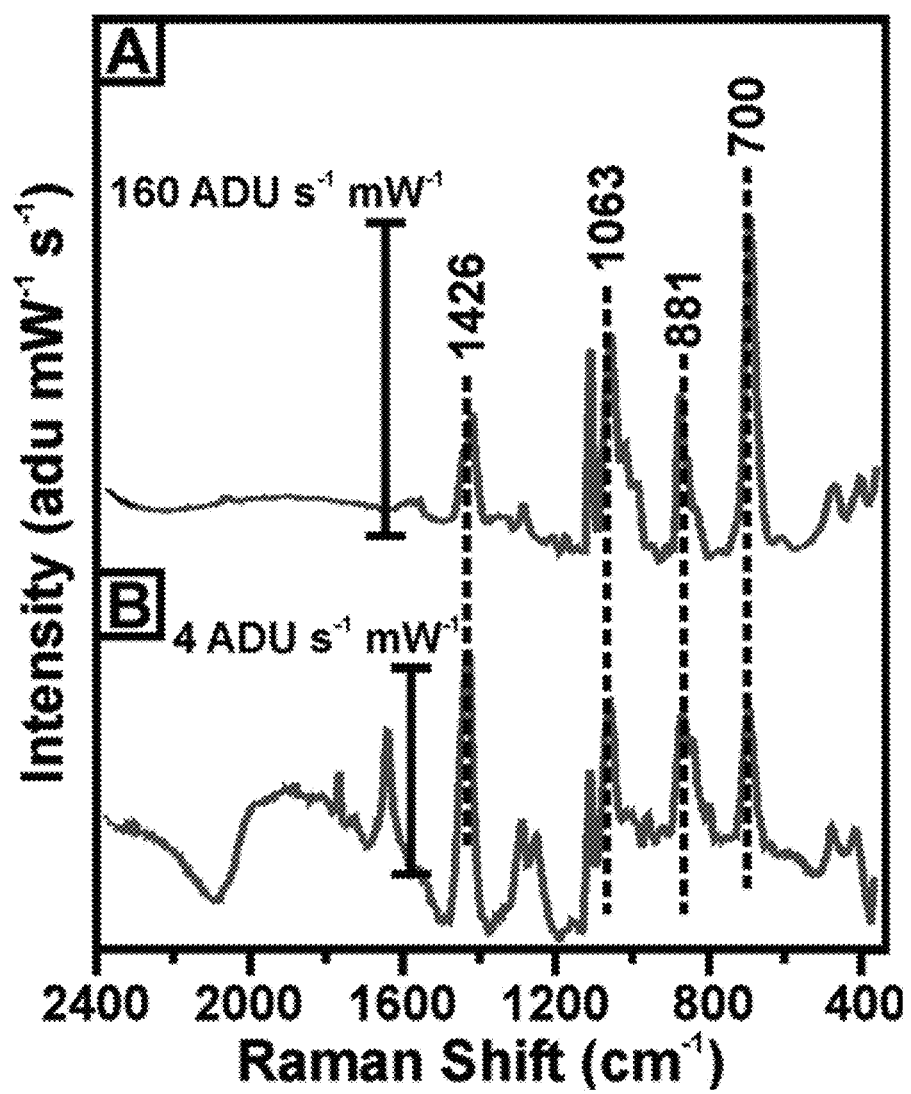
FIG. 2 shows a comparison of (A) normal SERS spectra and (8) in vivo transcutaneous SERSSORS spectra of a DT/MH-functionalized AgFON.

SESORS from SAM functionalized AgFON surfaces. In vivo transcutaneous SESORS spectra of a DT/MH functionalized AgFON were compared with the corresponding spectra of the functionalized AgFON taken with the spectrometer in standard mode. FIG. 2A shows the SER spectrum of a DT/MH AgFON. FIG. 2B shows the in vivo SESOR spectrum of an implanted DT/MH AgFON. Representative peaks can be seen at 1462, 1063, 881, and 700 cm$^{-1}$. The Maximum peak intensity was 160 ADD s$^{-1}$ mW$^{-1}$ in the standard SERS spectrum and 4 ADU S$^{-1}$ mW$^{-1}$ in the transcutaneous SORS spectrum. Thus the SERS signal is attenuated by approximately 95% due to the presence of skin; however, all spectral features from the DT/MH AgFON remain easily observable.

Figure 3:
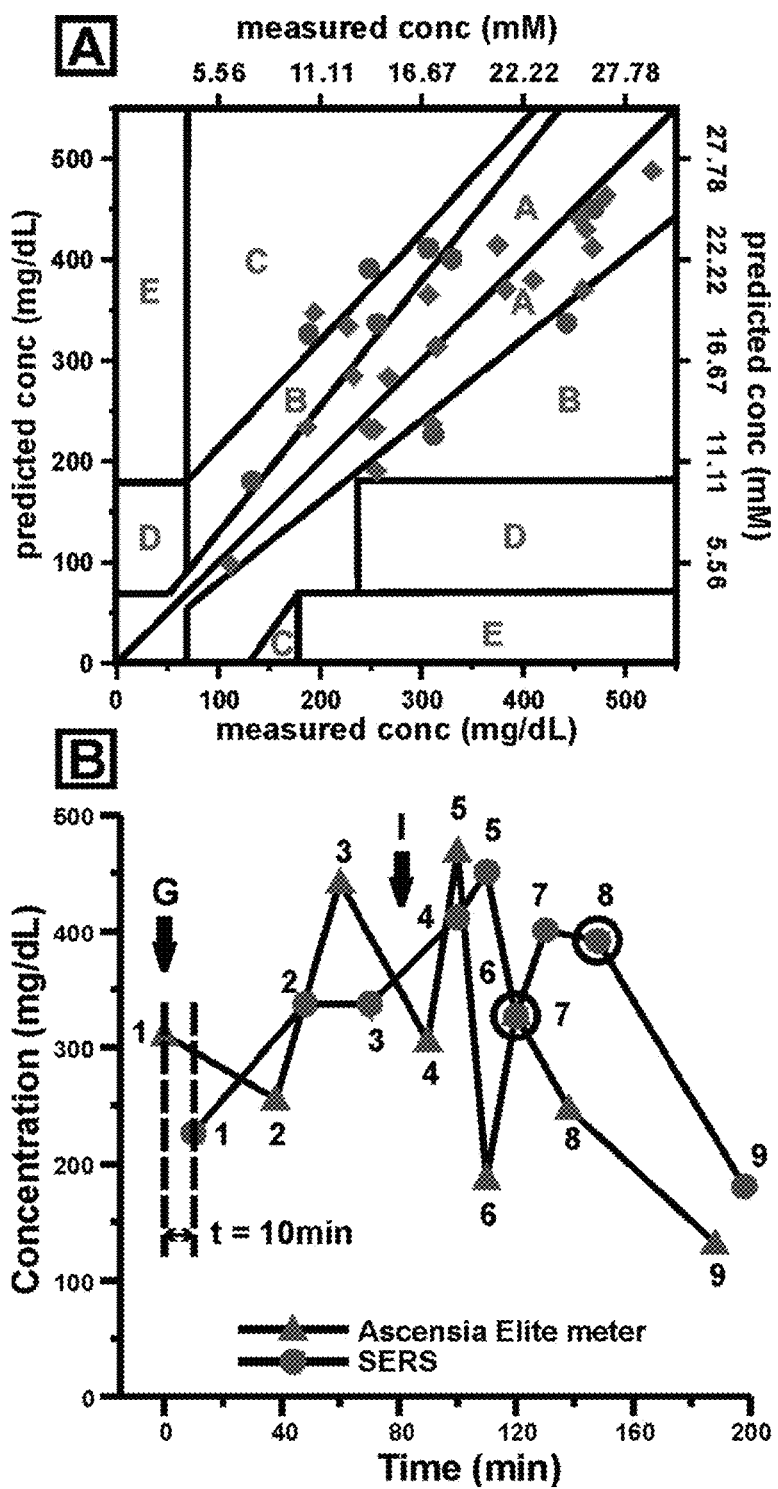
FIG. 3 shows: (A) Calibration (+) and validation (e) sets of the first in vivo transcutaneous SESORS glucose measurements. Twenty-one (21) measurements were used for calibration, 9 for validation. RMSEC=58.11 mg l d (3.32 mM) and RMSEP=96.35 mg l dL (5.35 roM). (B) Time-course of validation measurements. Glucose concentration is plotted with respect to time. Both the ASCENSIA ELITE and SERS measurements follow qualitative trends. Note—infusion of insulin (I) at 82 min.

Clarke error grid analysis and time course comparison. The Clarke error grid was introduced over 20 years ago (Clarke, W. L.; Cox, D.; Gonder-Frederick, L. A.; Carter, W.; Pohl, S. L. *Diabetes Care* 1987, 10, 622-628; herein incorporated by reference in its entirety) and has become a common standard to compare the accuracy and performance of glucose sensors (Clarke, W. L. *Diabetes Technol Ther* 2005, 7, 776-779; herein incorporated by reference in its entirety). Predicted concentrations are plotted versus measured concentrations and the graph is divided into five different zones. Measurements that fall in zone A are considered clinically accurate measurements, in zone B they lead to benign or no action by the patient, in zone C they lead to unnecessary action, in zone D they lead to a lack of action when glucose value correction is necessary, and, finally, in zone E they lead to actions that are opposite to those that are clinically necessary. Accurate sensing only results in data points within the A and B ranges of the grid (Sheffield, C. A.; Kane, M. P.; Bakst, G.; Busch, R. S.; Abelseth, J. M.; Hamilton, R. A. *Diabetes Technology & Therapeutics* 2009, 11, 587-592; herein incorporated by reference in its entirety). FIG. 3A shows a Clarke error grid analysis from in vivo transcutaneous SESORS glucose measurements. Unlike previous in vivo experiments, all measurements were not taken from a single position on the sensor, since using the annular fiber bundle to collect spectra inherently leads to spatially averaged collection from a circular area instead of a single point. In addition, no holder was required to secure the sensor in position and the sensor was allowed to move with the body of the rat as it breathed. Thus relative spatial motion between the sensor chip and the SORS probe was not problematic. In total, 30 measurements were taken. Twenty-one (21) data points were correlated with the ASCENSIA ELITE readings and used to create the calibration set. Nine (9) measurements were used as independent data points for the validation set. Seven (7) of the 9 validation points fell within the A and B ranges, showing good predictive results. Higher error (RMSEC=58.11 mg/dL (3.23 mM) and RMSEP=96.35 mg/dL (5.35 mM)) is seen than in previous in vivo results, but given the added optical dispersion of the skin and the displacement of the sensor during the experiment this is not unexpected. It should be noted that these RMSEC values are similar to those reported in earlier in vitro experiments.

FIG. 3B shows a comparison between readings of the ASCENSIA ELITE and SESORS measurements as a function of time. Though not quantitatively identical, both effectively track the decrease of glucose concentration after dosing with insulin. The quantitative discrepancy between the sensors can be explained in part by their different sensing environments. The Ascensia Elite measures blood glucose concentration while the SERS sensor detects the concentration of glucose in the interstitial fluid. It is agreed that there is a delay associated with diffusion of glucose from blood vessels into the interstitial fluid, though estimates are inexact (Wei, C.; Lunn, D. J.; Acerini, C. L.; Allen, J. M.; Larsen, A. M.; Wilinska, M. E.; Dunger, D. B.; Hovorka, R. *Diabetic Medicine* 2010, 27, 117-122; herein incorporated by reference in its entirety). Therefore, it is unsurprising that the predicted values of the Ascensia Elite and the SERS sensor do not quantitatively agree. Nevertheless, the extent of agreement is highly encouraging. In addition to the different environments that the two sensors sample, the use of the Ascensia Elite as the calibration method for the SERS measurements also contributed to the differences observed. The scatter in the SERS measurements incorporates the error inherent in the Ascensia Elite, increasing the perceived SERS error. The current standard for accuracy of home blood glucose monitoring systems (ISO 15197) states that device measurements should fall within 20% of laboratory standard results 95% of the time (this corresponds to Zone A in the Clarke Error Grid). This standard allows for large variations in glucose readings. Studies of commercial home glucose meters similar to the one used in these experiments have shown that most do not even meet this standard (Thomas, L. E.; Kane, M. P.; Bakst, G.; Busch, R. S.; Hamilton, R. A.; Abelseth, J. M. *Diabetes Technology & Therapeutics* 2008, 10, 102-110; herein incorporated by reference in its entirety). In a test of six home glucose meters, only one reached the ISO standard, with 96% of measurements falling within the A region. While the least accurate meter showed only 67% of measurements falling within the A region. In addition to accuracy, home glucose meter precision was also measured. The precision varied from 5.5%-8.4% (7.7-11.1 mg/dL) (Thomas, L. E.; Kane, M. P.; Bakst, G.; Busch, R. S.; Hamilton, R. A.; Abelseth, J. M. *Diabetes Technology & Therapeutics* 2008, 10, 102-110; herein incorporated by reference in its entirety). Due to the calibrating method used in this Example, the error in both the precision and the accuracy of the electrochemical sensing method contributed to even greater error in SERS measurements. These results show that the SERS sensor is viable in vivo and can detect glucose concentration fluctuations over time.

Example 2

In Vivo, Transcutaneous Glucose Sensing Using Surface-Enhanced Spatially Offset Raman Spectroscopy Materials. All the chemicals were reagent grade or better and used as purchased. Silver pellets (99.99%) were purchased from the Kurt J. Lesker Co. (Clairton, Pa.). Titanium was obtained from McMaster-Carr (Chicago, Ill.) and cut into 0.5 mm thick, 8 mm diameter disks. $NH_4OH$ (28-30% in $H_2O$), $H_2O_2$ (30% in $H_2O$), and ethanol were purchased from Fisher Scientific (Fairlawn, Va.) for cleaning substrates. Silica nanosphere solution (600 nm±10-15% diameter, 10.2% solid) was purchased from Bangs Laboratories, Inc. (Fishers, Ind.). Only ultrapure water (18.2 M cm−1) from a Millipore system (Marlborough, Mass.) was used for substrate preparation. Glucose, albumin from bovine serum (BSA), decanethiol (DT), and 6-mercapto-1-hexanol (MH) were purchased from Sigma-Aldrich (St. Louis, Mo.). Insulin (100 U/mL) was acquired from Eli Lilly (Indianapolis, Ind.).

AgFON fabrication and incubation procedure. The titanium substrates were cleaned by sonicating in a 5:1:1 H2O/H2O2/NH4OH solution. In previous studies, the nanosphere solution was directly dropcoated onto the titanium substrate (Stuart, D. A.; Yuen, J. M.; Lyandres, N. S. O.; Yonzon, C. R.; Glucksberg, M. R.; Walsh, J. T.; Van Duyne, R. P. *Analytical Chemistry* 2006, 78, 7211-7215; Lyandres, O.; Shah, N. C.; Yonzon, C. R.; Walsh, J. T.; Glucksberg, M. R.; Van Duyne, R. P. *Analytical Chemistry* 2005, 77, 6134-6139; Lyandres, O.; Yuen, J. M.; Shah, N. C.; VanDuyne, R. P.; Walsh, J. T.; Glucksberg, M. R. *Diabetes Technology & Therapeutics* 2008, 10, 257-265; Yuen, J. M.; Shah, N. C.; Walsh, J. T.; Glucksberg, M. R.; Van Duyne, R. P. *Analytical Chemistry* 2010, 82, 8382-8385; herein incorporated by reference in their entireties). In experiments conducted during development of embodiments of the present invention a fabrication technique was employed where silica nanospheres were first isolated from solution by centrifugation and removal of the supernatant. The nanospheres were then dispersed in ultrapure water and sonicated to disperse particle aggregates. This procedure ensured that a more uniform close-packed array of nanospheres formed on the titanium substrate surface. Approximately 20 μL of nanosphere solution was drop-coated onto each clean titanium substrate and allowed to dry under ambient conditions. An Ag film (200 nm thick) was deposited over the nanosphere mask using a thermal deposition system to form silver film over nanosphere (AgFON) substrates. The substrates were incubated in 1 mM DT in ethanol for 45 min and transferred to 1 mM MH in ethanol for at least 12 h to form a mixed DT/MH SAM. The AgFONs were kept in the 1 mM MH solution until used.

Instrumentation. The SESORS system described in Example 1 was used. The only alteration was the use of a 785 nm diode laser (Renishaw, RL785, 300 mW, <1 cm−1).

Surgical implantation. All surgical procedures followed protocols filed with the Northwestern University IACUC. Male Sprague-Dawley rats (300-500 g) were anesthetized with isoflurane (1.5-3%) throughout the surgical procedure and the duration of the experiment. The animal was checked for pain reactions by toe-tug and blink tests. None were observed. After the anesthetic had taken effect, the surgical areas were prepared by removal of hair (shaving and chemical depilatory) and cleaning. The femoral vein and artery were cannulated using PE 50 tubing for drug/glucose injections and blood glucose measurements, respectively. An incision was made in the skin and a pocket was blunt dissected into the subcutaneous space. A single DT/MH AgFON was placed in the pocket. All incisions were closed with surgical clips. The rats were thermally stabilized by an electric heating pad throughout the course of the surgery and experiment. Following the experiment, the animals were sacrificed with an overdose of sodium pentabarbitol (150 mg/kg) and bilateral thoracotomy.

Experimental procedure and spectroscopic measurement. The rats were placed in the SESORS apparatus. The glucose concentration in the rats was increased through intermittent intravenous infusion (1 g/mL in sterile saline) and decreased by N insulin injection (0.2 mL of 2 U/mL) over the course of experiments. A droplet of blood was drawn from the rats, the glucose level was measured with the OneTouch® Ultra® 2 home blood glucometer, and corresponding SESORS measurements were taken ($\lambda_{ex}$=785 nm, $P_{ex}$=50 mW, $t_{acq}$=2 min). To keep the osmotic pressure of the rats at normal physiological levels, a volume of BSA (0.8% in sterile saline) equal to the blood removed was injected following each blood glucose measurement via femoral cannula. The data were collected and analyzed by the partial least-squares leave-one-out (PLS-LOO) method. The calculations were performed with MATLAB (MathWorks, Inc., Natick, Mass.) and PLS_Toolbox (Eignevector Research, Inc., Manson, Wash.).

Figure 4:
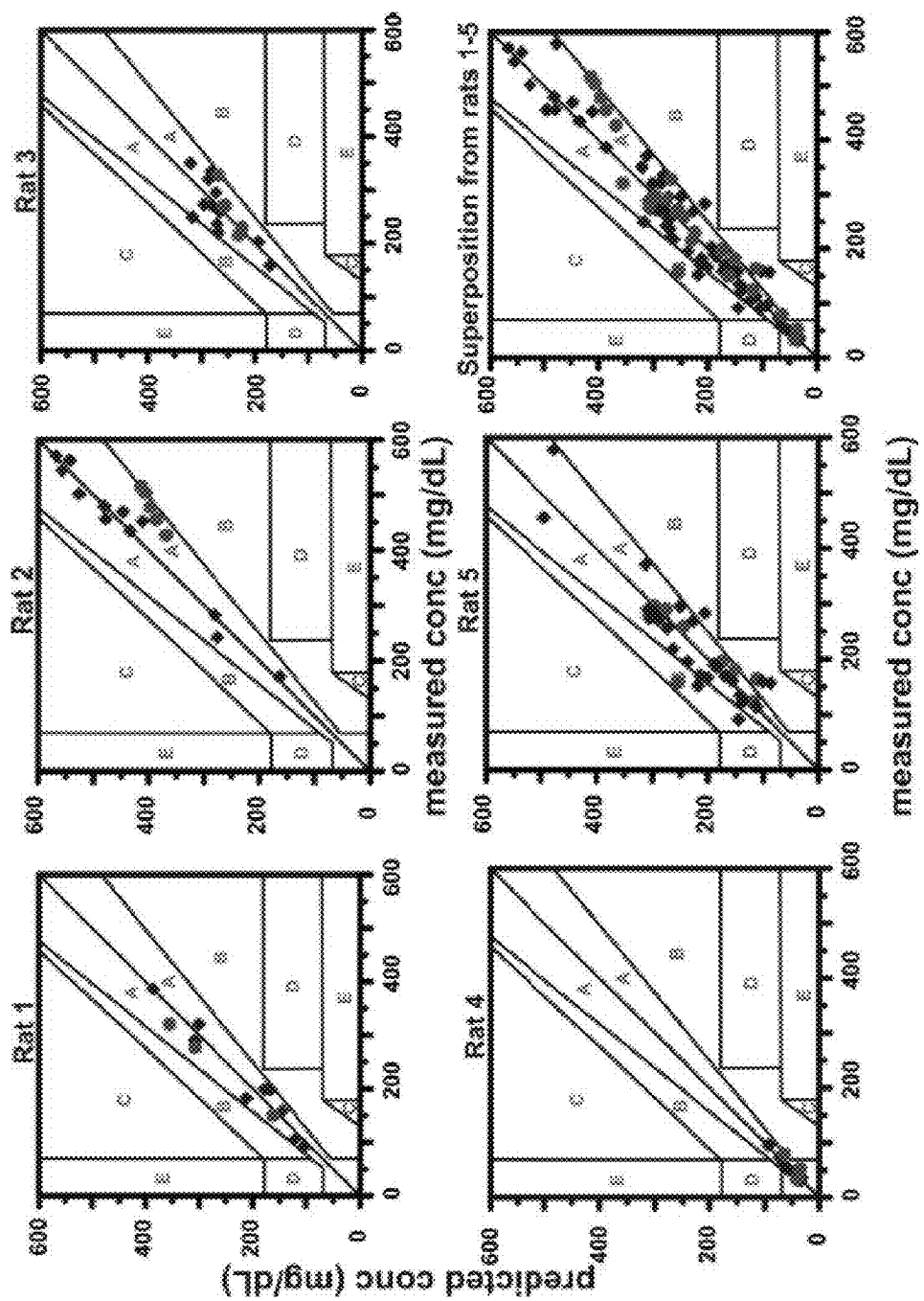
FIG. 4 shows calibration (□) and validation (●) data sets for in vivo transcutaneous SESORS glucose measurements on 5 rats. All data points were acquired with $\sigma_{ex}$=785 nm, $P_{ex}$=50 mW, $t_{acq}$=2 min.

Reliability and Hypoglycemic accuracy of SESORS in in vivo glucose sensing. The Clarke error grid has became the most common standard for evaluating the accuracy and performance of glucose sensors in clinically relevant concentration ranges (Clarke, W. L.; Cox, D.; Gonderfrederick, L. A.; Carter, W.; Pohl, S. L. *Diabetes Care* 1987, 10, 622-628; Clarke, W. L. *Diabetes Technology & Therapeutics* 2005, 7, 776-779); herein incorporated by reference in their entireties. The grid is divided into five zones with measured concentrations on the x-axis and predicted concentrations on the y-axis. Predictions that fall in these zones lead to the following: (A) clinically accurate measurements and treatment, (B) benign errors or no action, (C) unnecessary action, (D) a lack of action, and (E) actions that are opposite to those that are clinically necessary. Accurate measurements only result in data points within the A and B zone of the grid (Sheffield, C. A.; Kane, M. P.; Bakst, G.; Busch, R. S.; Abelseth, J. M.; Hamilton, R. A. *Diabetes Technology & Therapeutics* 2009, 11, 587-592; herein incorporated by reference in its entirety). Five separate in vivo transcutaneous SESORS glucose experiments are presented on Clarke error grids in FIG. 4. Measurements were taken from multiple spots of the implanted sensor due to movement of body of the rat as it breathed. The relative motion between the sensor and the SORS probe did not cause consistent problems due to the spatially averaged collection of the annular fiber bundle. The results of the five in vivo experiments are summarized in Table I.

TABLE I

Quantitative in vivo transcutaneous glucose detection using PLS calibration for five rats

| Rat number | Points used for Calibration | Points used for Validation | RMSEC | RMSEP | MARDC | MARDV |
|---|---|---|---|---|---|---|
| 1 | 9 | 3 | 20.4 mg/dL (1.1 mM) | 28.4 mg/dL (1.6 mM) | 10.9% | 10.3% |
| 2 | 12 | 5 | 20.6 mg/dL (1.1 mM) | 83.2 mg/dL (4.6 mM) | 4.13% | 17.0% |
| 3 | 14 | 5 | 35.3 mg/dL (2.0 mM) | 28.8 mg/dL (1.6 mM) | 10.8% | 7.40% |
| 4 | 9 | 3 | 3.6 mg/dL (0.2 mM) | 13.7 mg/dL (0.8 mM) | 6.84% | 24.0% |
| 5 | 27 | 9 | 43.1 mg/dL (2.4 mM) | 40.0 mg/dL (2.2 mM) | 16.2% | 16.0% |

For each experiment, all points of the calibration and validation fall in zone A and B range, indicating high sensor accuracy. Note that all points for rats 1-4 fall only within zone A. Both the mean absolute relative difference values for calibration and validation (MARDC and MARDV) and root mean square error for calibration and prediction (RMSEC and RMSEP) are lower than the previous in vivo transcutaneous results and comparable to the previous windowed chamber results (Yuen, J. M.; Shah, N. C.; Walsh, J. T.; Glucksberg, M. R.; Van Duyne, R. P. *Analytical Chemistry* 2010, 82, 8382-8385; Stuart, D. A.; Yuen, J. M.; Lyandres, N. S. O.; Yonzon, C. R.; Glucksberg, M. R.; Walsh, J. T.; Van Duyne, R. P. *Analytical Chemistry* 2006, 78, 7211-7215; herein incorporated by reference in their entireties). These improved results indicate that the refined fabrication technique for preparing the SERS substrates yields and improved glucose sensor. The new fabrication procedure for preparing AgFONs yields a more uniform, robust, and reproducibly close-packed array of nanospheres. This, in turn, yields a spatially more uniform surface plasmon resonance, higher SERS enhancement factors, and improved S/N for the SERS glucose sensor. For previous in vivo studies, the AgFONs used provided enhancement factors of 106. The refined process has increased the enhancement factors to mid-107 level, and possibly to 109 under optimal conditions.

The error can be further improved by increasing the number of data points in the calibration. In practice, the calibration model would be created with a large number of data points spanning the whole range of physically relevant glucose concentration (0-450 mg/dL). However, since only a limited number of data points can be collected from each rat due to the lifetime of the rat during an experiment, a specific ratio of calibration points to validation points was used to create a robust model. The ratio of calibration to validation points that is used in the studies described herein is between 2:1 and 3:1. Based on previous experiments, a ratio in this range builds a relatively accurate calibration model for validation. In the five in vivo transcutaneous SESORS glucose experiments, the data from rat 5 has a greater number of calibration points than the other four rats, but has higher error. This is because glucose concentrations span around two times the range in rat 5 than in other rats. A wider range of concentrations results in more variation in the spectra which leads to great error in the PLS-LOO calibration model. This error can be reduced by including even more data points in the calibration model. Nevertheless, the results from the five experiments show that the glucose sensor can make accurate and consistent in vivo transcutaneous glucose measurements.

Strict glycemic control benefits both diabetic and ICU patients (Kondepati, V. R.; Heise, H. M. *Analytical and Bioanalytical Chemistry* 2007, 388, 545-563; herein incorporated by reference in its entirety). Reliable CGM plays a key role in optimal glycemic control. To date, most commercially available CGM devices have 14-20% error range, and none of them can achieve 100% accuracy in terms of Clarke error grid analysis. In comparison, the SERS-based glucose sensor provides an accurate GCM sensor. 100% of measurements from all the rats are in the clinically acceptable range (zone A and B range). Moreover, the experiments demonstrated high accuracy for low glucose concentrations (31-79 mg/dL). At the center of diabetes management is prevention of hypoglycemia. However, the sensors available today have lower accuracy at low glucose levels than they do at higher levels, causing unreliable detection of hypoglycemia (Kondepati, V. R.; Heise, H. M. *Analytical and Bioanalytical Chemistry* 2007, 388, 545-563; Oliver, N. S.; Toumazou, C.; Cass, A. E. G.; Johnston, D. G. *Diabetic Medicine* 2009, 26, 197-210; Brauker, J. *Diabetes Technology & Therapeutics* 2009, 11, S25-S36; herein incorporated by reference in their entireties). The ISO/DIS 15197 requires that the sensor should detect a result within 15 mg/dL (0.83 mmol/L) for reference glucose values 75 mg/dL (4.2 mmol/L) and, the sensor should be within 20% for reference glucose values 75 mg/dL. The SERS-based sensor meets and exceeds the requirements of the standard.

Figure 5:
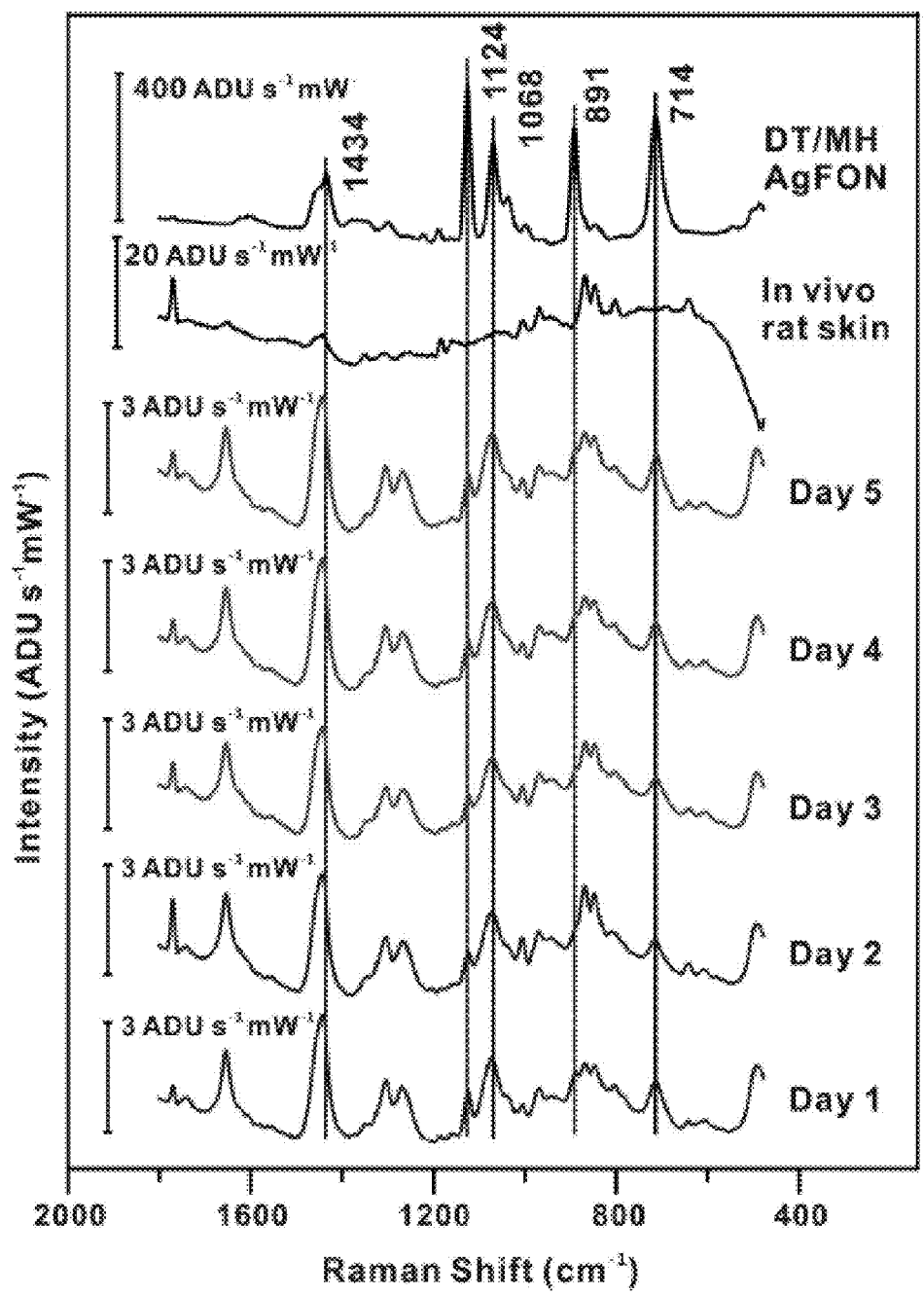
FIG. 5 shows a comparison of SESOR spectra from day 1-5, in vivo rat skin, and DT/MH-functionalized AgFON. $\sigma_{ex}$=785 nm, $P_{ex}$=50 mW, $t_{acq}$=2 min.
Figure 6:
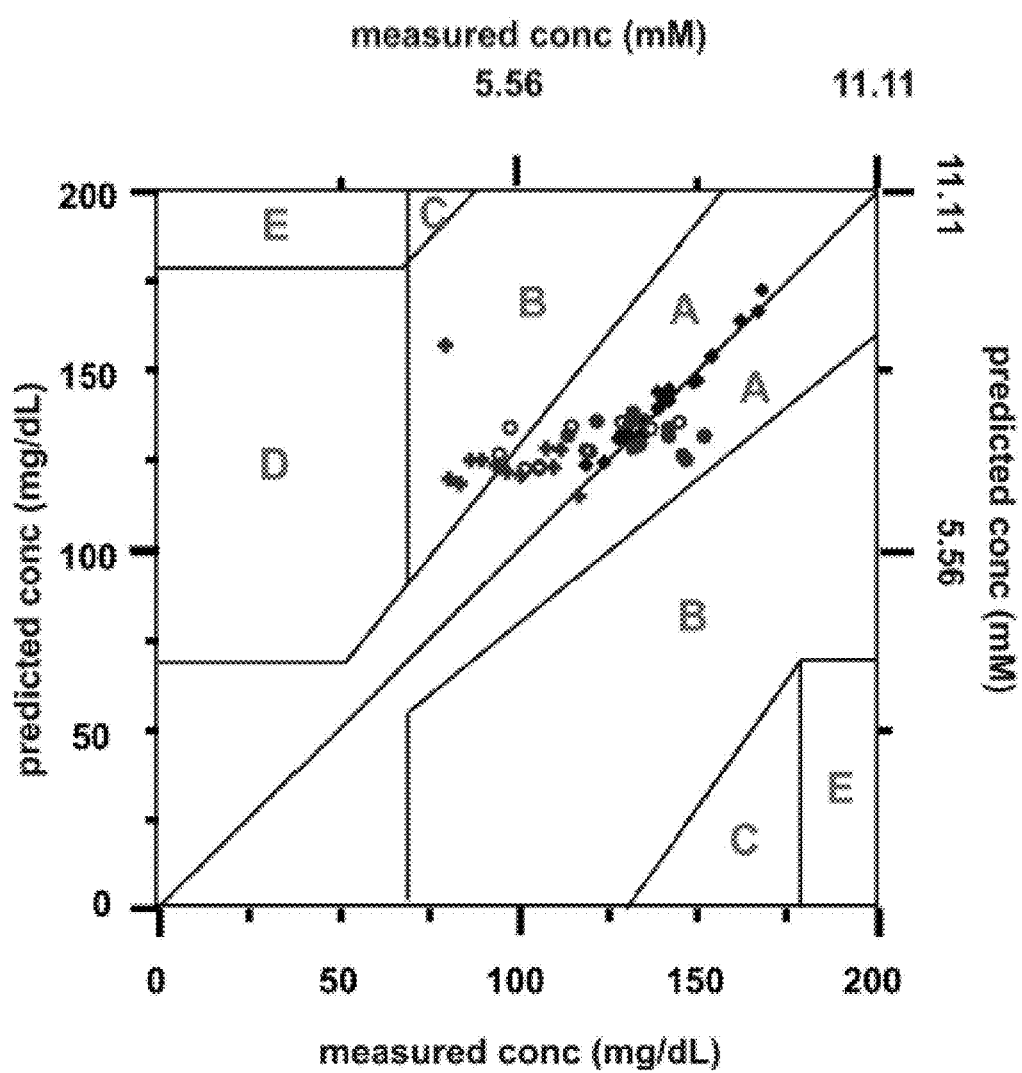
FIG. 6 shows calibration and validation data sets for a period of 5-day in vivo transcutaneous SESORS glucose measurements on one rat. Measurements from day 1 and 2 (□) were used for calibration sets. Measurements from day 3 (●), 4 (○) and 5 (□) were used for validation sets. All data points were acquired in vivo transcutaneously with λex=785 nm, Pex=50 mW, tacq=2 min.

Long term stability of SESORS in vivo glucose sensing. An implantable glucose sensor must be stable for at least 3 days for continuously in vivo glucose sensing (Kaufman, F. R.; Gibson, L. C.; Halvorson, M.; Carpenter, S.; Fisher, L. K.; Pitukcheewanont, P. *Diabetes Care* 2001, 24, 2030-2034; herein incorporated by reference in its entirety). Herein, the stability of the DT/MH functionalized AgFON for transcutaneously monitoring glucose was studied over a period of 20 days in a randomly chosen rat. For days 1-5, SESOR spectra were captured every hour for 12 hours a day from the same implanted sensor in the same rat with a laser beam at 785 nm yielding 50 mW at the sample ($t_{acq}$=2 min). One of the acquired SESOR spectra from each day is shown in FIG. 5. The DT/MH peaks are clearly present among the peaks of the rat skin in each day's spectrum as compared to the spectrum of in vivo rat skin and DT/MH AgFON. Representative peaks can be seen at 1434, 1124, 1068, 891, and 714 $cm_{-1}$. Peaks in the region between 1050 and 700 $cm_{-1}$ correspond to the skin and hair of the rat. Their positions and intensities varied across different days due to the regrowth of hair. Otherwise, the spectral band positions and intensities of each day's spectrum in other region did not vary significantly over the course of 5 days. To evaluate the accuracy and performance of our sensor over the first 5 days, the in vivo transcutaneous SESORS glucose measurements were analyzed by Clarke error grid as shown in FIG. 6. The measurements from the first 2 days were used as a calibration sets and those from the rest of the 3 days were used as a validation set. All calibration and validation points fall in zones A and B, showing excellent accuracy. The MARD and RMSE for calibration are 2.3 mg/dL (0.1 mM) and 1.42%, respectively. The results of the validation measurements for the remaining 3 days are summarized in Table II. Both MARD and RMSE for validation did not show a significant increase over the 3 days period, indicating good sensor stability.

TABLE II

Quantitative in vivo transcutaneous glucose detection using PLS calibration for 5-day monitoring

| Day | Measurement Number | Daily RMSEP | Daily MARDV | Overall RMSEP | Overall MARDV |
|---|---|---|---|---|---|
| 3 | 12 | 13.5 mg/dL (0.8 mM) | 8.32% | 13.5 mg/dL (0.8 mM) | 8.32% |
| 4 | 12 | 17.4 mg/dL (1.0 mM) | 13.3% | 15.6 mg/dL (0.9 mM) | 10.8% |
| 5 | 12 | 33.3 mg/dL (1.9 mM) | 31.6% | 23.0 mg/dL (1.3 mM) | 17.7% |

Figure 7:
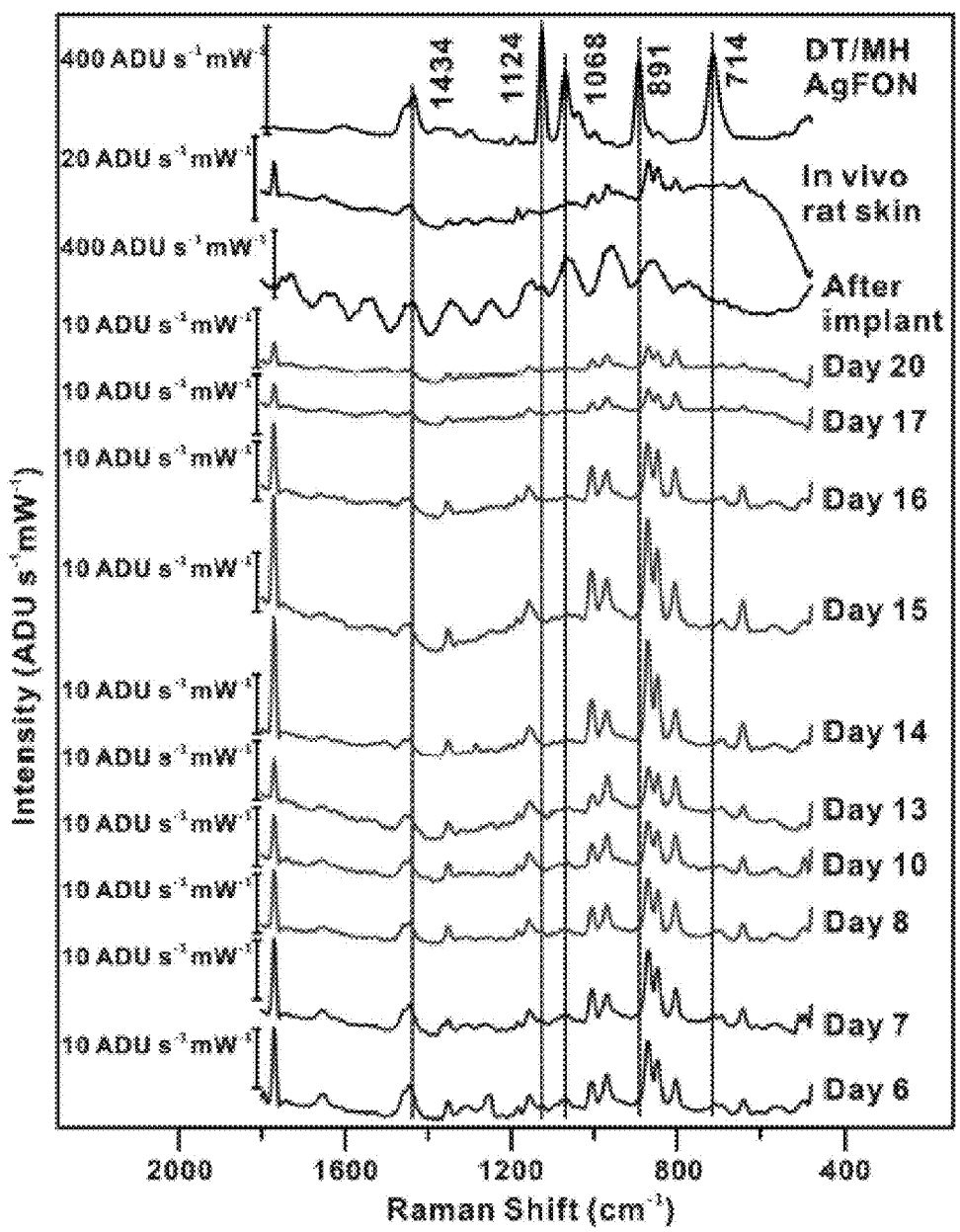
FIG. 7 shows a comparison of SESOR spectra from day 6-20, after implant, in vivo rat skin, and DT/MH-functionalized AgFON. $\sigma_{ex}$=785 nm, $P_{ex}$=2 mW, $t_{acq}$=2 min.
Figure 8:
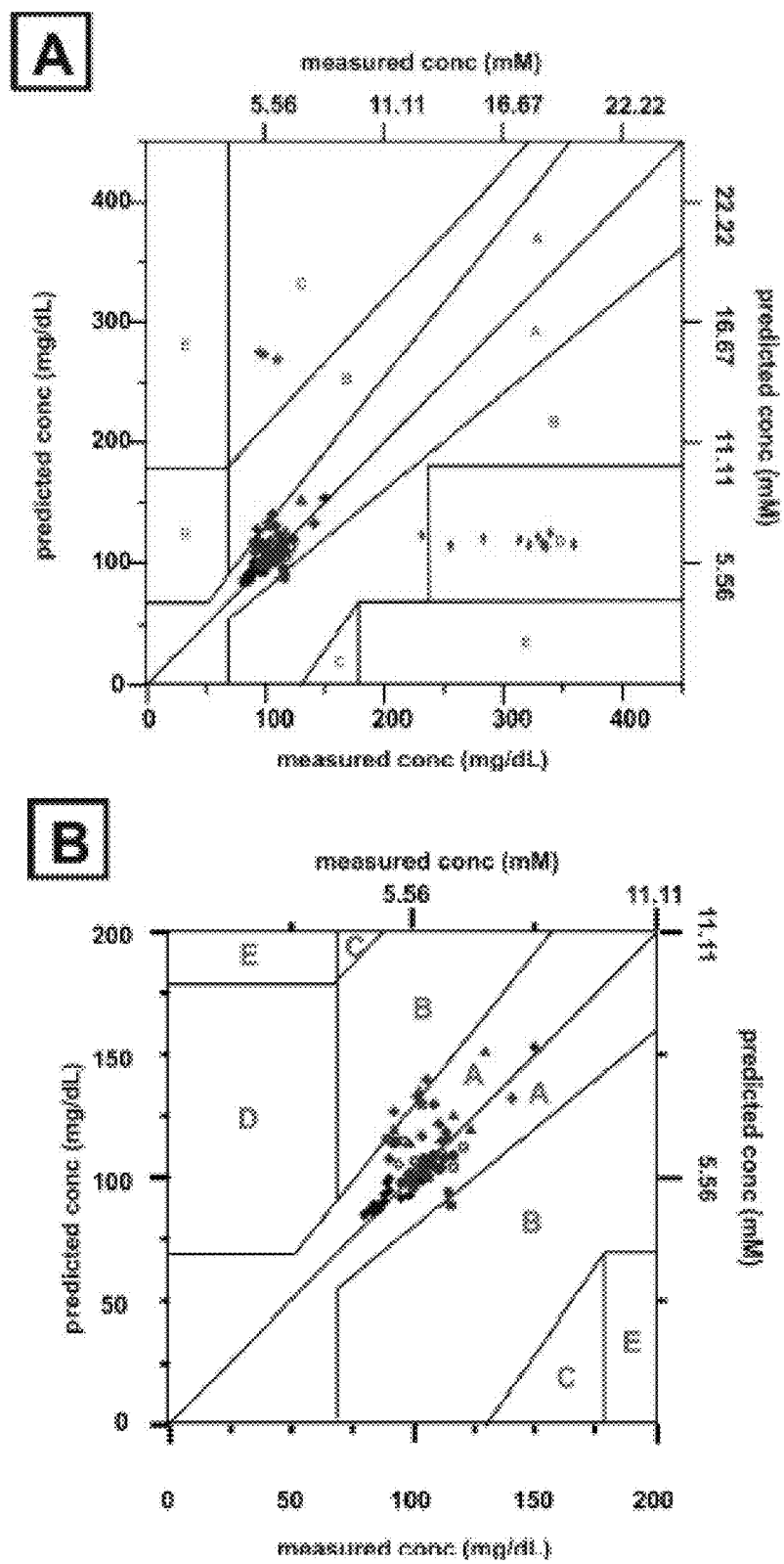
FIG. 8 shows calibration and validation data sets for a period of 12-day in vivo transcutaneous SESORS glucose measurements on one rat. Measurements from day 6 and 7 (□) were used for calibration sets. Measurements from day 8 (●), 10 (○), 13 (□), 14 (▲), 15 (□), 16 (□), 17 (□), 20 (□), and in vivo rat skin (□) were used for validation sets. All data points were acquired in vivo transcutaneously with σ ex=785 nm, Pex=2 mW, tacq=2 min.

For SESORS technique to be used as a practical approach in glucose sensing, the incident laser power on the skin must be below the safety level for skin exposure. To demonstrate that meaningful data can be collected at low laser power, starting on day 6 the incident power on the sample was attenuated to 2 mW, which is approximately an order of magnitude below the safe level for skin illumination in the NIR spectral region. For day 6-13, SESOR spectra were captured every hour for 12 hours each day from the same implanted sensor in the same rat ($\lambda_{ex}$=785 nm, $t_{acq}$=2 min). After day 13, four spectra were acquired each day (except day 16). FIG. 7 presents the representative SESOR spectra acquired from each day. As time progressed, the daily spectrum showed diminished DT/MH features and increased skin features. One DT/MH peak (891 $cm_{-1}$) does disappear after lowering the laser power due to obfuscation by hair and skin peaks, but this is somewhat expected with the lower signal intensity. The data collection was stopped at day 20 due to the significant change of spectral band positions and intensities. Glucose measurements from days 6 and 7 were used a calibration set and the measurements from the rest of days were used as a validation set (see FIG. 8). Measurements from days 6 to 17 fall in the zones A and B. Data from day 20 fell in zone C, indicating that our SERS glucose sensor functioned properly up to at least 17 days. In order to prove that the SERS sensor read glucose signals rather than random noises, ten SESOR spectra were taken from an area not over the implanted sensor. These ten measurements are also presented in FIG. 8. Nine of ten measurements fall in zone D, demonstrating our glucose sensor detects indeed glucose signal. The MARD and RMSE for calibration of 2 mW measurements are 4.2 mg/dL (0.2 mM) and 3.69%, respectively. The results of the validation measurements of the 2 mW illumination power for the rest of the days are summarized in Table III. Again, both MARD and RMSE for validation did not show significant increase over the 12 days period.

TABLE III

Quantitative in vivo transcutaneous glucose detection using PLS calibration for 12-day monitoring

| Day | Measurement Number | Daily RMSEP | Daily MARDV | Overall RMSEP | Overall MARDV |
|---|---|---|---|---|---|
| 8 | 12 | 11.2 mg/dL (0.6 mM) | 6.66% | 11.2 mg/dL (0.6 mM) | 6.66% |
| 10 | 12 | 12.5 mg/dL (0.7 mM) | 10.3% | 11.9 mg/dL (0.7 mM) | 8.49% |
| 13 | 12 | 20.1 mg/dL (1.1 mM) | 16.0% | 15.1 mg/dL (0.8 mM) | 11.0% |
| 14 | 4 | 7.7 mg/dL (0.4 mM) | 5.33% | 14.6 mg/dL (0.8 mM) | 10.4% |
| 15 | 4 | 23.4 mg/dL (1.3 mM) | 20.4% | 15.6 mg/dL (0.9 mM) | 11.4% |
| 16 | 1 | N/A | 24.2% | 15.9 mg/dL (0.9 mM) | 11.6% |
| 17 | 4 | 10.4 mg/dL (0.6 mM) | 7.13% | 15.3 mg/dL (0.9 mM) | 11.3% |

Overall, the SERS glucose sensor showed excellent accuracy and reliability over a period of 17 days. The longest life span of GCM sensors currently available on the market is 7 days. Although some long-term implanted sensors showed longer functional time, they do not function well during the first 3-4 weeks after implantation due to the foreign body response (Gilligan, B. C.; Shults, M.; Rhodes, R. K.; Jacobs, P. G.; Brauker, J. H.; Pintar, T. J.; Updike, S. 2010, 39, 609-624; herein incorporated by reference in its entirety). In contrast, the SERS sensor functions immediately after implantation, indicating that the foreign body response does not affect the glucose sensing ability of the sensor. Furthermore, the SERS sensor was calibrated just once during both the 5-day and 12-day measurements. One of the main disadvantages of current GCM devices is that repeated calibration is needed for obtaining reliable glycemic profiles.$_{28}$ Most of the devices need calibration at least four times a day (Kondepati, V. R.; Heise, H. M. *Analytical and Bioanalytical Chemistry* 2007, 388, 545-563; herein incorporated by reference in its entirety). The accuracy of the sensor is greatly affected by the number and timing of the calibrations. The SERS sensor showed consistent accuracy during the multiple days measurement period with only one calibration at the initial stage of sensor utilization.

Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the present invention.

REFERENCES

All publications and patents listed below and/or mentioned in the above specification are herein incorporated by reference.

Kneipp, K.; Kneipp, H.; Kartha, V. B.; Manoharan, R.; Deinum, G.; Itzkan, I.; Dasari, R. R.; Feld, M. S. *Physical Review E* 1998, 57, R6281-R6284.

Das, G.; Mecarini, F.; Gentile, F.; De Angelis, F.; Kumar, H. G. M.; Candeloro, P.; Liberale, C.; Cuda, G.; Di Fabrizio, E. *Biosensors & Bioelectronics* 2009, 24, 1693-1699.

Stuart, D. A.; Yuen, J. M.; Lyandres, N. S. O.; Yonzon, C. R.; Glucksberg, M. R.; Walsh, J. T.; Van Duyne, R. P. *Analytical Chemistry* 2006, 78, 7211-7215.

Xie, W.; Qiu, P. H.; Mao, C. B. *Journal of Materials Chemistry* 2011, 21, 5190-5202.

Bantz, K. C.; Meyer, A. F.; Wittenberg, N. J.; Im, H.; Kurtulus, O.; Lee, S. H.; Lindquist, N. C.; Oh, S. H.; Haynes, C. L. *Physical Chemistry Chemical Physics* 2011, 13, 11551-11567.

Stuart, D. A.; Yonzon, C. R.; Zhang, X. Y.; Lyandres, O.; Shah, N. C.; Glucksberg, M. R.; Walsh, J. T.; Van Duyne, R. P. *Analytical Chemistry* 2005, 77, 4013-4019.

Zhang, X. Y.; Zhao, J.; Whitney, A. V.; Elam, J. W.; Van Duyne, R. P. *Journal of the American Chemical Society* 2006, 128, 10304-10309.

Stiles, P. L.; Dieringer, J. A.; Shah, N. C.; Van Duyne, R. R. In *Annual Review of Analytical Chemistry*; Annual Reviews: Palo Alto, 2008; Vol. 1, pp 601-626.

Wustholz, K. L.; Henry, A. I.; McMahon, J. M.; Freeman, R. G.; Valley, N.; Piotti, M. E.; Natan, M. J.; Schatz, G. C.; Van Duyne, R. P. *Journal of the American Chemical Society* 2010, 132, 10903-10910.

Henry, A. I.; Bingham, J. M.; Ringe, E.; Marks, L. D.; Schatz, G. C.; Van Duyne, R. P. *Journal of Physical Chemistry C* 2011, 115, 9291-9305.

Huang, G. G.; Han, X. X.; Hossain, M. K.; Ozaki, Y. *Analytical Chemistry* 2009, 81, 5881 5888.

Singhal, R.; Bhattacharyya, S.; Orynbayeva, Z.; Vitol, E.; Friedman, G.; Gogotsi, Y. *Nanotechnology* 2010, 21.

Lyandres, O.; Shah, N. C.; Yonzon, C. R.; Walsh, J. T.; Glucksberg, M. R.; Van Duyne, R. P. *Analytical Chemistry* 2005, 77, 6134-6139.

Matousek, P.; Clark, I. P.; Draper, E. R. C.; Morris, M. D.; Goodship, A. E.; Everall, N.; Towrie, M.; Finney, W. F.; Parker, A. W. *Applied Spectroscopy* 2005, 59, 393-400.

Matousek, P.; Morris, M. D.; Everall, N.; Clark, I. P.; Towrie, M.; Draper, E.; Goodship, A.; Parker, A. W. *Applied Spectroscopy* 2005, 59, 1485-1492.

Matousek, P.; Draper, E. R. C.; Goodship, A. E.; Clark, I. P.; Ronayne, K. L.; Parker, A. W. *Applied Spectroscopy* 2006, 60, 758-763.

Stone, N.; Baker, R.; Rogers, K.; Parker, A. W.; Matousek, P. *Analyst* 2007, 132, 899-905.

Stone, N.; Faulds, K.; Graham, D.; Matousek, P. *Analytical Chemistry* 2010, 82, 3969-3973.

Stone, N. S. N.; Kerssens, M.; Lloyd, G. R.; Faulds, K.; Graham, D.; Matousek, P. *Chemical Science* 2011, 2, 776-780.

Qian, X. M.; Peng, X. H.; Ansari, D. O.; Yin-Goen, Q.; Chen, G. Z.; Shin, D. M.; Yang, L.; Young, A. N.; Wang, M. D.; Nie, S. M. *Nature Biotechnology* 2008, 26, 83-90.

Zavaleta, C. L.; Smith, B. R.; Walton, I.; Doering, W.; Davis, G.; Shojaei, B.; Natan, M. J.; Gambhir, S. S. *Proceedings of the National Academy of Sciences of the United States of America* 2009, 106, 13511-13516.

Lewinski, N.; Colvin, V.; Drezek, R. *Small* 2008, 4, 26-49.

Oberdorster, G.; Stone, V.; Donaldson, K. *Nanotoxicology* 2007, 1, 2-25.

Murphy, C. J.; Gole, A. M.; Stone, J. W.; Sisco, P. N.; Alkilany, A. M.; Goldsmith, E. C.; Baxter, S. C. *Accounts of Chemical Research* 2008, 41, 1721-1730. Atlanta, Ga., 2011.

Cryer, P. E. *Diabetologia* 2002, 45, 937-948.

*Diabetes Care* 2011, 34 Suppl 1, S11-61.

Kondepati, V. R.; Heise, H. M. *Analytical and Bioanalytical Chemistry* 2007, 388, 545-563.

Oliver, N. S.; Toumazou, C.; Cass, A. E. G.; Johnston, D. G. *Diabetic Medicine* 2009, 26, 197-210.

Brauker, J. *Diabetes Technology & Therapeutics* 2009, 11, S25-S36.

Aye, T.; Block, J.; Buckingham, B. *Endocrinology and Metabolism Clinics of North America* 2010, 39, 609-624.

Buckingham, B. A.; Kollman, C.; Beck, R. W.; Kalajian, A.; Fiallo-Scharer, R.; Tansey, M. J.; Fox, L. A.; Wilson, D. M.; Weinzimer, S. A.; Ruedy, K. J.; Tamborlane, W. V.; DirecNet Study, G. *Diabetes Technology & Therapeutics* 2006, 8, 318-325.

Renard, E. *Current Opinion in Pharmacology* 2002, 2, 708-716.

Gilligan, B. C.; Shults, M.; Rhodes, R. K.; Jacobs, P. G.; Brauker, J. H.; Pintar, T. J.; Updike, S. J. *Diabetes Technology & Therapeutics* 2004, 6, 378-386.

Dingari, N. C.; Barman, I.; Singh, G. P.; Kang, J. W.; Dasari, R. R.; Feld, M. S. *Analytical and Bioanalytical Chemistry* 2011, 400, 2871-2880.

Lipson, J.; Bernhardt, J.; Block, U.; Freeman, W. R.; Hofmeister, R.; Hristakeva, M.; Lenosky, T.; McNamara, R.; Petrasek, D.; Veltkamp, D.; Waydo, S. *J Diabetes Sci Technol* 2009, 3, 233-241.

Enejder, A. M. K.; Scecina, T. G.; Oh, J.; Hunter, M.; Shih, W. C.; Sasic, S.; Horowitz, G. L.; Feld, M. S. *Journal of Biomedical Optics* 2005, 10.

Lyandres, O.; Van Duyne, R. P.; Walsh, J. T.; Glucksberg, M. R.; Mehrotra, S. *Analyst* 2010, 135, 2111-2118.

Lyandres, O.; Yuen, J. M.; Shah, N. C.; VanDuyne, R. P.; Walsh, J. T.; Glucksberg, M. R. *Diabetes Technology & Therapeutics* 2008, 10, 257-265.

Yuen, J. M.; Shah, N. C.; Walsh, J. T.; Glucksberg, M. R.; Van Duyne, R. P. *Analytical Chemistry* 2010, 82, 8382-8385.

Clarke, W. L.; Cox, D.; Gonderfrederick, L. A.; Carter, W.; Pohl, S. L. *Diabetes Care* 1987, 10, 622-628.

Clarke, W. L. *Diabetes Technology & Therapeutics* 2005, 7, 776-779.

Sheffield, C. A.; Kane, M. P.; Bakst, G.; Busch, R. S.; Abelseth, J. M.; Hamilton, R. A. *Diabetes Technology & Therapeutics* 2009, 11, 587-592.

Greeneltch, N.; Dieringer, J. A.; Van Duyne, R. P. In *in preparation*; Northwestern University: Evanston, 2011.

Kaufman, F. R.; Gibson, L. C.; Halvorson, M.; Carpenter, S.; Fisher, L. K.; Pitukcheewanont, P. *Diabetes Care* 2001, 24, 2030-2034.

Boisselier, E.; Astruc, D. *Chemical Society Reviews* 2009, 38, 1759-1782.

Feng, S. Y.; Lin, J. Q.; Cheng, M.; Li, Y. Z.; Chen, G. N.; Huang, Z. F.; Yu, Y.; Chen, R.; Zeng, H. S. *Applied Spectroscopy* 2009, 63, 1089-1094.

Huang, W. E.; Li, M. Q.; Jarvis, R. M.; Goodacre, R.; Banwart, S. A In *Advances in Applied Microbiology, Vol 70*; Elsevier Academic Press Inc: San Diego, 2010; Vol. 70, pp 153-186.

Kneipp, J; Kneipp, H.; Wittig, B.; Kneipp, K. *Nanomedicine-Nanotechnology Biology and Medicine* 2010, 6, 214-226.

Qian, X. M.; Peng, X. H.; Ansari, D. O.; Yin-Goen, Q.; Chen, G. Z.; Shin, D. M.; Yang, L.; Young, A N.; Wang, M. D.; Nie, S. M, *Nature Biotechnology* 2008, 26, 83-90.

Zavaleta, C. L.; Smith, B. R; Walton, 1; Doering, W.; Davis, G.; Shojaei, B.; Natan, M. I; Gambhir, S. S. *Proceedings of the National Academy of Sciences of the United States of America* 2009, 106, 13511-13516.

Shafer-Peltier, K. E.; Haynes, C. L.; Glucksberg, M. R.; Van Duyne, R. P. *Journal of the American Chemical Society* 2003, 125, 588-593.

Shah, N. C.; Lyandres, O.; Yonzon, C. R; Walsh, J. T.; Glucksberg, M. R; Van Duyne, R. P. *Analytical Chemistry* 2005, 77, 6134-6139.

Stuart, D. A; Yuen, J.; Shah, N. C.; Lyandres, O.; Yonzon, C. R; Glucksberg, M. R.; Walsh Jr., J. T.; Van Duyne, R. P. *Anal. Chem* 2006.

Yonzon, C. R.; Haynes, C. L.; Zhang, X. Y.; Walsh, J. T.; Van Duyne, R. P. *Analytical Chemistry* 2004, 76, 78-85.

Anderson, R. R; Parrish, J. A. *Journal of Investigative Dermatology* 1981, 77, 13-19.

Bashkatov, A. N.; Genina, E. A.; Kochubey, V. I.; Tuchin, V. V. *Journal of Physics D-Applied Physics* 2005, 38, 2543-2555.

Nielsen, K.; Zhao, L. S., J J; Stamnes, K.; Moam, J. In *Solar Radiation and Human Health*; Bjertness, E., Ed.; The Norvegian Academy of Science and Letters: Oslo, 2008.

Matousek, P. *Chemical Society Reviews* 2007, 36, 1292-1304.

Matousek, P.; Stone, N. *Analyst* 2009, 134, 1058-1066.

Shah, N. C.; Lyandres, O.; Walsh, J. T.; Glucksberg, M. R.; Van Duyne, R. P. *Analytical Chemistry* 2007, 79, 6927-6932.

Clarke, W. L.; Cox, D.; Gonder-Frederick, L. A.; Carter, W.; Pohl, S. L. *Diabetes Care* 1987, 10, 622-628.

Clarke, W. L. *Diabetes Technol Ther* 2005, 7, 776-779.

Wei, C.; Lunn, D. J.; Acerini, C. L.; Allen, J. M.; Larsen, A. M.; Wilinska, M. E.; Dunger, D. B.; Hovorka, R. *Diabetic Medicine* 2010, 27, 117-122.

Thomas, L. E.; Kane, M. P.; Bakst, G.; Busch, R. S.; Hamilton, R. A.; Abelseth, J. M. *Diabetes Technology & Therapeutics* 2008, 10, 102-110.

Barone, P. W.; Parker, R. S.; Strano, M. S. *Analytical Chemistry* 2005, 77, 7556-7562.

Barone, P. W.; Strano, M. S. *J Diabetes Sci Technol* 2009, 3, 242-252.

Heller, A.; Feldman, B. *Chemical Reviews* 2008, 108, 2482-2505.

Wustholz, K. L.; Henry, A.-I.; McMahon, J. M.; Freeman, R. G.; Valley, N.; Piotti, M. E.; natan, M. J.; Schatz, G. C.; Van Duyne, R. P. *Journal of the American Chemical Society* 2010, 132, ACS ASAP July 21.

We claim:

1. A method for quantification of an analyte in vivo, comprising:
    a) acquiring, through the skin of a subject, a spatially offset Raman spectrum from a biosensor implanted under the skin of said subject, wherein said biosensor comprises a plurality of nanospheres and a metal film over said nanospheres; and
    b) quantifying the concentration of an analyte in said subject based on said spatially offset Raman spectrum.

2. The method of claim 1, wherein said acquiring step comprises the steps of: (1) illuminating said biosensor at least one first spot with light; (2) collecting Raman scattering light from said biosensor at a at least one second spot in response to illumination by said light, wherein each second spot is apart from the at least one first spot so as to define a source-detection (S-D) offset distance.

3. The method of claim 1, wherein said biosensor further comprises a substrate, wherein said substrate comprises copper or titanium, and wherein said plurality of nanobiosensors are adherent to said substrate.

4. The method of claim 1, wherein said acquiring step is performed with at least one of a spectrograph and a CCD camera.

5. The method of claim 2, wherein said acquiring step is performed with a probe having a working end and in-line filters placed on said working end.

6. The method of claim 5, wherein said probe comprises: (a) at least one first fiber positioned over said at least one first spot for delivering the light thereto; and (b) at least one second fiber.

7. The method of claim 2, further comprising the step of acquiring a Raman spectrum from said at least one first spot illuminated with said light.

8. The method of claim 1, wherein said biosensor is fully implanted in said subject.

9. The method of claim 1, wherein said biosensor further comprises a self-assembled partition layer formed on said surface of said metal film over said nanospheres.

10. The method of claim 1, wherein said nanospheres comprise polystyrene or silica nanospheres.

11. The method of claim 1, wherein said analyte is glucose.

12. The method of claim 1, wherein said metal film comprises silver.

13. A system comprising:
    a) a surface enhanced Raman biosensor configured to be implanted in a subject, wherein said biosensor comprises
       a plurality of nanospheres and a metal film over said nanospheres; and
    b) a sensing device configured for collecting spatially offset Raman spectra from said biosensor when said biosensor is implanted in a subject.

14. The system of claim 13, further comprising: c) a light source capable of illuminating said biosensor through tissue of said subject.

15. The system of claim 13, wherein said sensing device comprises a spectrograph and/or CCD camera.

16. The system of claim 13, wherein said sensing devices comprises a probe having a working end and in-line filters placed on said working end.

17. The system of claim 13, wherein said biosensor further comprises: a self-assembled partition layer formed on said surface of said metal film over said nanospheres.

18. The system of claim 13, wherein said biosensor further comprises a substrate, wherein said substrate is copper or titanium, and wherein said plurality of nanobiosensors are adherent to said substrate.

19. The system of claim 13, wherein said nanospheres comprise polystyrene or silica nanospheres.

20. The system of claim 13, wherein said analyte is glucose.

* * * * *